US012790578B2

(12) United States Patent
Hakemeyer et al.

(10) Patent No.: US 12,790,578 B2
(45) Date of Patent: Nov. 10, 2026

(54) GROWTH CONTROL OF EUKARYOTIC CELLS

(71) Applicant: HOFFMANN-LA ROCHE INC., Little Falls, NJ (US)

(72) Inventors: Christian Hakemeyer, Ilvesheim (DE); Heino Buentemeyer, Bielefeld (DE)

(73) Assignee: Hoffman-La Roche, Inc., Little Falls, NJ (US)

(*) Notice: Subject to any disclaimer, the term of this patent is extended or adjusted under 35 U.S.C. 154(b) by 1790 days.

(21) Appl. No.: 16/467,723

(22) PCT Filed: Dec. 20, 2017

(86) PCT No.: PCT/EP2017/083886
§ 371 (c)(1),
(2) Date: Jun. 7, 2019

(87) PCT Pub. No.: WO2018/115161
PCT Pub. Date: Jun. 28, 2018

(65) Prior Publication Data

US 2020/0063086 A1 Feb. 27, 2020

(30) Foreign Application Priority Data

Dec. 21, 2016 (EP) .................................... 16205982

(51) Int. Cl.
*C12M 1/36* (2006.01)
*C12M 1/34* (2006.01)
(Continued)

(52) U.S. Cl.
CPC ............ *C12M 41/48* (2013.01); *C12M 41/12* (2013.01); *C12M 41/36* (2013.01); *C12Q 3/00* (2013.01); *B01J 19/0013* (2013.01)

(58) Field of Classification Search
CPC ...... C12M 41/12; C12M 41/36; C12M 41/38; B01J 9/0013; C12Q 3/00
(Continued)

(56) References Cited

U.S. PATENT DOCUMENTS 5,976,833 A 11/1999 Furukawa et al.
2009/0104594 A1 4/2009 Webb
(Continued)

FOREIGN PATENT DOCUMENTS

CN 1110316 A 10/1995
CN 101443444 A 5/2009
(Continued)

OTHER PUBLICATIONS

Aehle et al., Increasing batch-to-batch reproducibility of CHO-cell cultures using a model predictive control approach, Cytotechnology, (vol. 64, (2012), pp. 623-634.*
(Continued)

*Primary Examiner* — Jennifer M.H. Tichy
(74) *Attorney, Agent, or Firm* — Harness, Dickey & Pierce, P.L.C.

(57) ABSTRACT

The system is configured to receive a target cell density and a target time and for each of a plurality of time intervals; receive a measured cell density of the eukaryotic cells in the culture medium of the first tank; compute a predicted cell density at target time as a function of at least the measured cell density; compare the predicted cell density and the target cell density; adjusting the temperature of the culture medium in the first tank if the predicted cell density deviates from the target cell density by increasing the temperature by 0.1° C. to 1° C. if the predicted cell density is lower than the target cell density; or by decreasing the temperature by 0.1° C. to 1° C. if the predicted cell density is higher than the target cell density.

16 Claims, 16 Drawing Sheets

(51) Int. Cl.
*C12Q 3/00* (2006.01)
*B01J 19/00* (2006.01)

(58) Field of Classification Search
USPC .......................................................... 435/383
See application file for complete search history.

(56) References Cited

U.S. PATENT DOCUMENTS

| | | | | |
|---|---|---|---|---|
| 2010/0159524 | A1 | 6/2010 | Smith et al. | |
| 2015/0247794 | A1* | 9/2015 | Olesberg .................. | C12Q 3/00 250/339.07 |

FOREIGN PATENT DOCUMENTS

| | | | |
|---|---|---|---|
| CN | 102482633 | A | 5/2012 |
| CN | 102549142 | A | 7/2012 |
| EP | 0661380 | A2 | 7/1995 |
| JP | S63-188384 | A | 8/1988 |
| JP | H7-184634 | A | 7/1995 |
| JP | H9-75077 | A | 3/1997 |
| JP | 2003-235544 | A | 8/2003 |
| JP | 2008-526203 | A | 7/2008 |
| WO | WO-2006/071716 | A2 | 7/2006 |
| WO | WO-2008/118500 | A1 | 10/2008 |
| WO | WO-2015/165583 | A1 | 11/2015 |

OTHER PUBLICATIONS

Notice of Reasons for Rejection dated Oct. 4, 2021 issued in corresponding Japanese patent application No. 2019-530766.

Decision of Rejection dated May 11, 2022 issued in corresponding Japanese patent application No. 2019-530766.

Justin Moretto et al.: "Process Raman Spectroscopy for In-Line CHO Cell Culture Monitoring", American Pharmaceutical Review, vol. 14, Apr. 2011 (Apr. 1, 2011).

International Preliminary Report on Patentability for corresponding PCT Application No. PCT/EP2017/083886 dated Jul. 4, 2019.

Klaus Joeris, "*In-situ microscopy: Online process monitoring of mammalian cell cultures*," Cytotechnology 38: 129-134, 2002.

Patrick Gammell, "*Initial identification of low temperature and culture stage induction of miRNA expression in suspension CHO-K1 cells*," Journal of Biotechnology, vol. 130, Issue 3, Juen 30, 2007, pp. 213-218. (abstract only).

Office Action for Chinese Application No. 201780073779.1 dated Jul. 18, 2022 and English translation.

International Search Report PCT/ISA/210 for International Application No. PCT/EP2017/083886 Dated Apr. 18, 2018.

Written Opinion of the International Searching Authority PCT/ISA/237 for International Application No. PCT/EP2017/083886 dated Apr. 18, 2018.

* cited by examiner

Batch 6; Temperature 36.5°C >> 35°C >> 34°C >> 32°C >>

GROWTH CONTROL OF EUKARYOTIC CELLS

CROSS-REFERENCE TO RELATED APPLICATIONS

This application is a national phase under 35 U.S.C. § 371 of PCT International Application No. PCT/EP2017/083886 which has an International filing date of Dec. 20, 2017, which claims priority to European Application No. 16205982.8, filed Dec. 21, 2016, the entire contents of each of which are hereby incorporated by reference.

FIELD OF THE INVENTION

The invention relates to the field of biotechnology, and more particularly to the field of controlling the growth of cells, in particular eukaryotic cells.

BACKGROUND AND RELATED ART

Therapeutically or commercially important proteins are often produced by cultivating mammalian cells containing a nucleic acid that encodes a recombinant protein of interest. For example, seed train processes are used to generate a sufficient number of mammalian cells to inoculate a large production bioreactor that is actually used to produce and harvest the protein of interest. Conventional seed train processes start with a small cell sample, e.g. a cryo-conserved cell bank vial, followed by multiple cell culture expansion steps in a progressively larger culture vessels or tanks.

Batch and fed-batch production processes comprise an unproductive growth phase, when cell mass accumulates, and a more productive stationary phase, when the majority of the protein or other bio-product is generated inside or outside of the cells. Although the growth phase and the stationary phase can also be observed in prokaryotic cells, the two different phases are of particular relevance for the cultivation of eukaryotic cells as the bio-products generated by eukaryotic cells are particularly sensitive to the metabolic state of the producing cell (which may for instance have an impact on the glycosylation pattern of a protein product).

Growing cells in a cell culture is a process that is very sensitive to many different factors: small differences in the composition of the culture medium or the nutritive solutions, small differences in the cell density of a cell sample used for inoculating a bioreactor, or an inaccurate calibration of various devices which measure process parameters like pH, temperature, oxygen or carbon dioxide concentration, can result in significant differences regarding the growth rate of the cells, regarding the amount of protein produced by each cell and even regarding the chemical composition or modification of the product. Proteins generated by eukaryotic cells are subject to many different biochemical modification processes such as glycosylation, phosphorylation, and others. Any change in the process parameters and growth condition may have a significant impact on the cell metabolism and thus may also have an impact on the glycosylation pattern of the generated protein. For example, Gammell P, Barron N, Kumar N, Clynes M (2007) in "Initial identification of low temperature and culture stage induction of miRNA expression in suspension CHO-K1 cells". J Biotechnol 130:213-218 have identified miR-21, a growth inhibitory miRNA, as being up-regulated during stationary phase growth induced either by temperature shift to low temperature or during normal batch culture. Thus, changing the temperature in a running eukaryotic cell culture project may have an impact on cell state.

US 2009/0104594 A1 describes a bioreactor that includes a sensor linked to a model free adaptive controller or optimizer. The sensor can provide a real time measurement of a quantity that correlates with final product titer or other desired product quality attribute. In addition, a method of culturing living cells is described. The method includes incubating the cells in a vessel, measuring a plurality of onditions inside the vessel, comparing the plurality of measurements, individually, to a plurality of setpoints with a model-free adaptive controller, and adjusting a condition inside the vessel based on at least one comparison.

In the context of cultivating eukaryotic cells, pharmaceutical companies therefore try to keep the process parameters as constant as possible to ensure a reproducible and safe production of the desired bio-product in a defined time interval.

Often, eukaryotic cells are grown under two different temperature conditions for the growth phase and for the stationary phase: the growth phase is typically performed at 37° C. while the production phase is typically performed by lowering the temperature to about 34° C. and keeping the temperature constantly at 34° C. throughout the production process in order to ensure a standardized, reproducible production process, a standardized product concentration and quality at the end of the production process. Likewise, the temperature is kept constant during the growth phase to ensure reproducibility of the process.

Thus, state of the art approaches for cultivating eukaryotic cells are based on keeping the cultivation parameters, in particular the temperature, constant (at least throughout the growth phase and the stationary phase, respectively).

However, as small variations in the initial cell density, medium composition and calibration properties of measuring devices cannot be avoided completely, there still exists a variability regarding the duration of cell culture projects and the total amount of bio-product that can be harvested after a given time period that makes it very difficult for biotechnical and pharmaceutical companies to plan the production process.

SUMMARY

It is an objective of the present invention to provide for an improved method and system for controlling the growth of cells as specified in the independent claims. Embodiments of the invention are given in the dependent claims. Embodiments of the present invention can be freely combined with each other if they are not mutually exclusive.

In one aspect, the invention relates to a method for controlling the growth of eukaryotic cells. A control logic receives a target cell density and a target time. The target cell density represents a desired cell density of the eukaryotic cells at the target time. The target time represents a future point in time. The eukaryotic cells are cultivated in a culture medium of a first tank. The method comprises, for each of a plurality of time intervals (e.g. at start or end of each time interval):

- measuring the cell density of the eukaryotic cells in the culture medium;
- computing, by the control logic, a predicted cell density at the target time as a function of at least the measured cell density;
- comparing, by the control logic, the predicted cell density and the target cell density;

adjusting, by the control logic, the temperature of the culture medium in the first tank if the predicted cell density deviates from the target cell density. The adjustment is performed either by increasing the temperature by 0.1° C. to 1° C. if the predicted cell density is lower than the target cell density; or by decreasing the temperature by 0.1° C. to 1° C. if the predicted cell density is higher than the target cell density.

Said features may be advantageous as they allow actively controlling the growth of eukaryotic cells to yield a defined number of cells at a defined point in time. It has been surprisingly observed that, although the temperature was not kept constant while growing the cell culture, the desired cell density was reached at the target time for many different cell culture projects even in case the starting conditions (starting temperature, starting cell concentration) were slightly different. Although eukaryotic cells and their metabolism are highly sensitive to changes in the environmental temperature, it has been observed that the generated bio-product does not differ from the bio-product generated under constant temperature conditions, at least not as long the temperature adjustments do not exceed 1° C. temperature difference per prediction time interval and do not exceed or drop below a physiologically tolerable temperature range.

Moreover, it has been observed that the cells tolerate and are able to quickly recover from temperature changes in the above specified temperature range. Thus, the overall time for a cell culture project is not prolonged by adjusting the temperature of the medium in the above specified temperature range. This is different for the adjustment of other production parameters, e.g. the pH, which have been observed to reduce the efficiency of cell production as the cells have been observed to require some additional time to recover from pH changes before they can continue accumulating cell mass and producing the desired bio-product.

By repeatedly predicting the time when a currently grown cell culture will probably reach a desired cell density, comparing the predicted time with a specified target time and by adapting the temperature of the cell culture medium accordingly, embodiments of the invention allow to compensate for small variations in the starting conditions of a cell culture and may allow to ensure that a cell culture will reach a desired cell density and will deliver a desired amount of bio-product at a particular, defined future time ("target time"). Depending on the cell line, the culture medium, the conditions in the tank, and the type of bio-product that is produced, the typical duration of a cell culture project starting from the inoculation of the cell culture to the time when the cell culture has reached the target cell density will vary. Many projects have a typical duration in a range of 3 to 5 days, e.g. 4.5 days. It has been observed that embodiments of the invention may compensate for up to 20% deviation of one or more process parameters at start time from the "typical" or "reference" process parameters of a reference cell culture project. For example, if a reference project was run at a constant temperature of 37° C. and required exactly 4 days (96 hours) until a desired cell density was reached, embodiments of the invention using the dynamic, prediction-based temperature adaptation approach, may allow to achieve the same cell density in a 20% shorter time interval, i.e., within 3.2 days (77 hours). Likewise, in case the amount of cells used for inoculating the bioreactor was 20% below the amount of cells used for inoculating the reference bioreactor, the dynamic temperature adaptation according to embodiments of the invention may allow for compensating the reduced number of starting cells and provide the desired cell density at the desired target time.

Likewise, embodiments of the invention have been observed to successfully compensate for several sources of error (failure of the oxygen or nutrients supply, failure of the pH control system, etc) which would have—based on conventional, constant temperature cell cultivation techniques—resulted in a decrease of product or cell density of up to 20%.

Thus, embodiments of the invention may allow compensating system failures and process parameter deviations relative to a reference culture project and thus may allow for a better control and predictability of a cell culture project.

The computation of the predicted cell density at the target time as a function of at least the measured cell density can be performed based on the currently measured cell density only. Preferentially, the cell density at the target time is predicted as a function of multiple measured cell densities having been measured in earlier time intervals.

According to preferred embodiments, the temperature adjustments do not decrease the temperature of the culture medium below a temperature of 32° C. and do not increase the temperature of the culture medium about the temperature of 38° C.

Performing temperature adjustments only within said temperature range may be beneficial as it has been observed that temperature adjustments within said range may affect the growth rate in a controlled manner but do not significantly shift the cell metabolism in direction of other metabolic pathways, e.g. of producing heat shock proteins. Temperature adjustments within said range have been observed to be fully and quickly reversible as cells do not need extra time for recovering from a previously used temperature.

According to embodiments, the method for controlling cell growth and the adjustment of the temperature, if necessary, is performed throughout the whole growth phase or throughout the whole stationary phase or throughout the growth and stationary time.

This may be beneficial as the longer the time span used for dynamically adjusting the temperature of the cell culture the better the ability to compensate for failures of system components and sub-optimal starting conditions.

According to embodiments, the first tank comprises a meter for performing online measurements of the cell density in the culture medium. Accordingly, the cell densities of the eukaryotic cells which are measured at each of the plurality of time intervals are online-measurements.

For example, measurement devices which measure the dielectric properties of the culture medium for determining the number of cells in a given volume of the medium or optical techniques, e.g. in the form of an online microscope, can be used for automatically counting the living cells in the medium can be used.

For instance, the FOGALE Biomass System can be used for determining the cell density in the tank without taking a sample. Using a dielectricity sensor has the advantage that-unlike optical techniques—the system is not sensitive to gas bubbles, cell debris and other particles in suspension. By making use of the FOGALE biomass sensor or similar sensor devices, the viable biomass concentration (Biovolume) can be determined as an online measurement independently of cell size variation.

Another example for an online cell density meter is an in-situ microscope. An in-situ microscope is a system developed to acquire images of mammalian cells directly inside a bioreactor (in-situ) during a cell culture project. It requires only minimal operator intervention. An example for an in-situ microscope and its use is described in Joeris K1, Frerichs J G, Konstantinov K, Scheper T: "In-situ microscopy: Online process monitoring of mammalian cell cultures" Cytotechnology. 2002 January; 38(1-3):129-34. doi: 10.1023/A:1021170502775.

A further example for an online cell density meter is a Raman spectrometer. The use of Raman spectrometers for the determination of cell densities in bioreactors has been described e.g. by Justin Moretto et al. in "Process Raman Spectroscopy for In-Line CHO Cell Culture Monitoring" (April 2011 issue of *American Pharmaceutical Review*—Volume 14).

Performing an online measurement of the cell density may have the advantage of avoiding problems associated with offline measurement: offline-measurement data tends to be of low quality due to significant latency times between the moment of measurement and the moment of performing a respective control operation. Moreover, the sampling process for obtaining the measurement value from a sample may increase the risk of an infection of the cell culture with undesired germs and may reduce the accuracy of the measurement due to sampling effects (e.g. a change in temperature).

In a further beneficial aspect, using online cell densities rather than offline densities allows for a fully automated cell culture growth control. Furthermore, using online cell densities may provide a large number of cell density measurements during a cell culture project and may thus provide a better data basis for predicting the cell density at the target time which again may increase prediction accuracy.

According to embodiments, the control logic is configured to terminate at least the adjusting of the temperature upon fulfillment of a termination criterion. The termination criterion can be, for example, the determination that the target time has been reached, or that the measured cell density is equal to or larger than the target cell density.

Optionally, the control logic may not only stop adjusting the temperature but may also stop the growing of the cell culture. For example, the control logic may send one or more control commands to automated control elements which cause the control elements to stop feeding and aerating the cells in the cell culture tank and start an automated cell harvesting process. Alternatively, the control logic sends a message to one or more mobile communication devices of the qualified technical staff to inform the staff that the cells in the tank must be harvested or further processed. In addition, or alternatively, the message is displayed on a screen operatively coupled to the control logic. The further processing may comprise transferring the cells or the whole culture medium comprising the cells from the first tank to a different, preferentially larger tank, e.g. another pre-production bioreactor or a production bioreactor. Depending on the embodiment, the harvesting process and/or the transfer process can be performed manually, automatically or semi-automatically.

Preferentially, repeated prediction of the future cell density at the target time, the comparison with the target time and the adjustment of the temperature, if necessary, is performed fully automatically. According to preferred embodiments, also the repeated transfer of cells from one pre-production tank to another pre-production tank or to a production tank and the final harvesting of the cells or the generated bio-product is performed fully automatically, i.e., without any human intervention. This may be advantageous as a fully automated system and method may be provided that is robust against slight variations in the starting conditions, robust against system component failures during the cell cultivation phase and that is able to reliably deliver a defined cell density and a defined product quality at a specified future time without any human intervention.

According to embodiments, the control logic receives a cell concentration deviation threshold for adjusting the temperature. The control logic adapts the temperature of the culture medium in the first tank only in case the predicted cell concentration at target time deviates by more than said threshold from the target cell concentration. This may be beneficial as the threshold introduces some inertia in the control loop and ensures that the temperature is adapted only in case the deviation from the target cell concentration is predicted to reach a significant level. For example, the control logic receives a lower cell concentration deviation threshold, e.g. 95% of the target cell density, and may increase the temperature of the medium in the first tank only in case the predicted cell concentration is lower than 95% of the target cell concentration. In addition, or alternatively, the control logic receives an upper cell concentration deviation threshold, e.g. 105% of the target cell density, and may decrease the temperature of the medium in the first tank only in case the predicted cell concentration is higher than 105% of the target cell concentration. Other lower and upper threshold values may likewise be used, e.g. 99% and 101%, or 98% and 102%, or asymmetric threshold values like 99% for the lower cell density threshold and 105% for the upper cell density threshold.

According to embodiments, the control logic provides a graphical user interface (GUI). The GUI enables a user to enter the target time and the target cell density before the control logic starts to compute the predicted cell densities. The GUI enables the user to modify the target time and/or the target cell density while the control logic computes the predicted cell densities at the plurality of time intervals.

According to some embodiments, the method further comprises transferring the culture medium of the first tank and the eukaryotic cells contained therein from the first tank to a second tank after the target cell density was reached. The second tank is larger than the first tank. The control logic receives a further target cell density and a further target time. The further target cell density represents a desired cell density of the eukaryotic cells at the further target time. As the further growth control process in the second tank is performed after the cells in the first tank reached the target cell density, the further target time represents a time later than the time of transferring the cells to the second tank.

For instance, the control logic can receive the target cell density, the further target density, the target time and/or the further target time directly from the user via a locally (on the same machine as the control logic) installed GUI or from a remotely installed GUI via a network. Alternatively, the control logic can read said (further) target times and target cell density from a configuration file having been created or modified by a user before the control logic was instantiated.

The transferred eukaryotic cells are then cultivated in the second tank. For each of a plurality of further time intervals (e.g. at the beginning or end of each time interval), the following sub-method is performed:

- measuring the cell density of the eukaryotic cells in a culture medium of the second tank;
- computing, by the control logic, a further predicted cell density at the further target time as a function of at least said measured cell density;
- comparing, by the control logic, the further predicted cell density and the further target cell density;

adjusting, by the control logic, the temperature of the culture medium in the second tank if the further predicted cell density deviates from the further target cell density. The adjusting is performed by increasing the temperature by 0.1° C. to 1° C. if the further predicted cell density is lower than the further target cell density. If the further predicted cell density is higher than the further target cell density, the control logic decreases the temperature by 0.1° C. to 1° C.

Depending on the embodiment, the first and second target cell densities may be identical or may differ from each other.

According to some embodiments, the first and second tanks respectively are bioreactors configured for growing the cell culture as batch-culture. The method is used in a seed train cultivation process for generating a defined minimum number of cells for the inoculation of a production bioreactor.

This may be advantageous as the cell culture can be grown to a first target cell density at a first target time semi- or fully automatically. Then, the cell culture can be transferred to another, larger tank, e.g. a further pre-production bioreactor or vessel. Then, the cells are grown to a second target cell density at a further, second target time. Said steps may be repeated for three, four or even more pre-production vessels or bioreactors until a sufficient number of cells is obtained for inoculating a large production bioreactor. Thus, the method may be used to grow a cell culture in a seed train culture project.

According to embodiments, the first tank is a bioreactor configured for growing the cell culture as a pre-production batch-culture. The second tank is larger than the first tank and is a bioreactor configured for growing the cell culture as a production culture.

The production culture can be, for example, a fed-batch culture. In some embodiments, the production culture can also be a batch culture.

According to embodiments, the eukaryotic cells are mammalian cells, in particular Chinese hamster ovary (CHO) cells. Alternatively, the eukaryotic cells are baby hamster kidney (BHK) cells or a human cell line. An example for a human cell line is Per.C6, a cell line derived by immortalizing human embryonic retina cells with the E1 gene of adenovirus. They are often used for producing monoclonal antibodies (MAbs) using G418 as the selection agent. Further, the eukaryotic cells may be NS0 cells, Sp2/0 cells, COS cells, K562 cells or HEK cells.

All embodiments described herein can likewise be used for controlling the growth of prokaryotic cells, in particular bacteria cells, e.g. *Escherichia coli* cells.

According to embodiments, the culture medium in the first tank has a volume of 500 liters or less.

According to embodiments, the method further comprises, for of each of the plurality of time intervals (e.g. at the start or end of each time interval):

defining a current observation interval for the current time interval, the current observation interval having a predefined length and terminating at the end of the current time interval; and receiving all cell densities having been measured during the current observation interval.

The predicted cell density is computed as a function of at least the measured cell density. The computation comprises extrapolating the cell densities measured during the current observation interval until the target time.

For example, the control logic may define the current observation interval by determine a current time provided by a clock and by analyzing a configuration file or a user input for determining the length of the observation interval. The control logic then identifies the current observation time interval as a time interval that ends at the current time and begins the determined length ahead of the current time. Examples of observation intervals determined at different current times are described in FIG. 2.

According to embodiments, the extrapolation comprises performing a curve fitting operation or a regression analysis on the cell densities measured during the current observation time.

According to embodiments, all time intervals of the plurality of time intervals are of equal length.

According to embodiments, all time intervals of the plurality of time intervals are of different length.

According to embodiments, the method comprises determining if the current time is close to the target time. For example, the control logic may determine that the current time is close to the target time in case a) a predefined duration since the inoculation of the culture medium has lapsed or in case b) a predefined number of predictions of the cell density at the target time has already been performed or c) that a predefined percentage of the target cell density has been reached or d) a predefined time before the target time has been reached, e.g. 13 hours before the target time (typically, said predefined time before the target time is in a range of 12 h-14 h). Other ways of automatically determining whether the current time is close to the target time exist. Alternatively, the user is enabled via the GUI to enter an indication that the current time is close to the target time.

In response to determining that the current time is close to the target time, the control logic reduces the length of all future ones of the plurality of time intervals.

This may be beneficial as the accuracy of the cell density prediction and the accuracy of the growth control may be increased: at the end of the cultivation time, the cell density is already high and small errors in a prediction in combination with long time intervals between the predictions may result in a failure to exactly produce the desired cell density at the target time. In order to increase accuracy of prediction and growth control, embodiments of the invention use shorter prediction time intervals at the end of a culture project. For example, the shortening of the prediction time intervals can be performed fully automatically be the control logic as described above or can be performed manually by a user.

According to embodiments, each of the plurality of time intervals has a duration of less than 30 minutes, preferentially less than 10 minutes. For example, each of the time intervals has a duration in the range of 1 minute to 10 minutes.

According to embodiments, the predefined length of the observation interval is in a range of 60 minutes to 480 minutes, in particular 80 to 100 minutes, e.g. 90 minutes.

It has been observed that the above durations of prediction time intervals and observation intervals provide a good compromise between high prediction accuracy and resource consumption (obtaining measurement values, making a prediction and comparing the predicted cell densities may consume processing power and generate network traffic, and the updating of a screen comprising a curve showing measured and predicted cell densities may further consume network, memory and CPU capacities).

According to embodiments, the culture medium in the first tank (and optionally also in the second tank and other tanks) is a CD-CHO AGT medium. However, the suitable medium strongly depends on the cell type, on the phase of cell growth (e.g. growth phase or stationary phase), on the type of product to be produced, the type of vessel or bioreactor used and on other factors. Therefore, the other media can be used also, e.g. DMEM, RPMI, Hams F12 and others.

According to a further embodiment, the adjusting of the temperature comprises increasing the temperature by 0.1° C. to 0.5° C., preferentially by 0.1° C. to 0.2° C. or decreasing the temperature by 0.1° C. to 0.5° C., preferentially by 0.1° C. to 0.2° C.

According to embodiments, the GUI or another component of the control system enables a user to enter additional control parameters before and/or during a running cell culture project. For example, the user can be enabled to specify the length of the prediction time intervals, the length of the observation intervals, the length of an adjustment interval, upper and/or lower threshold values for considering a predicted cell density to be (sufficiently) lower or higher than the target cell density, and/or the amount of temperature adjustment per adjustment action. Preferentially, the user is enabled to enter different values for positive temperature adjustment steps and negative temperature adjustment steps. This may a better adaptation of the temperature control to the heating and cooling characteristics of the bioreactor.

In a further aspect, the invention relates to a method for providing eukaryotic cells at a desired cell density at a defined future time. The method comprises entering, by a human user, the desired cell density and the future time via an interface of a control logic. The desired cell density represents a desired cell density of the eukaryotic cells at the entered future time. The control logic is used for controlling the growth of eukaryotic cells according to a method of any one of the embodiments described herein. The growth control is performed such that the entered desired cell density is used as the target cell density, the entered future time is used as the target time, and the eukaryotic cells are provided at the target cell density at the target time.

In a further aspect, the invention relates to a system for controlling the growth of eukaryotic cells. The system is to be controlled such that it yields a defined number of cells at a defined future time. The system comprises a control logic and a processor configured for executing the control logic. The control logic is operatively coupled to a first tank comprising eukaryotic cells in a culture medium. The control logic is configured for receiving a target cell density and a target time. For example, the target cell density and the target time can be received from a network interface, can be read from a configuration file of the control logic or can be received as user input via a graphical user interface. The target cell density represents a desired cell density of the eukaryotic cells at the target time. The target time represents a future point in time.

The system is configured to perform, for of each of a plurality of time intervals (e.g. at start or end of each time interval), a sub-method comprising:

- receiving a measured cell density of the eukaryotic cells in the culture medium of the first tank;
- computing a predicted cell density at target time as a function of at least the measured cell density;
- comparing the predicted cell density and the target cell density;
- adjusting, by the control logic, the temperature of the culture medium in the first tank if the predicted cell density deviates from the target cell density; if the predicted cell density is lower than the target cell density, the control logic increases the temperature by 0.1° C. to 1° C.; if the predicted cell density is higher than the target cell density, the control logic decreases the temperature by 0.1° C. to 1° C.

According to embodiments, the system further comprises the first tank and optionally also one or more further tanks (the further tanks may receive the cell culture from the first or another tank once the cells have reached a desired cell density in a previously used tank).

According to embodiments, the first tank comprises a meter for performing online measurements of the cell density in the culture medium. The cell densities of the eukaryotic cells measured at each of the plurality of time intervals are online-measurements.

According to embodiments, the control logic is configured to terminate at least the adjusting of the temperature upon a termination criterion being fulfilled. The termination criterion can be, for example, that the target time has been reached or that the measured cell density is equal to or larger than the target cell density.

According to embodiments, the system or one of its components, e.g. the control logic, is configured to providing a graphical user interface (GUI). The GUI enables a user to enter the target time and the target cell density before the control logic starts to compute the predicted cell densities. The GUI can also enable the user to modify the target time and/or the target cell density while the control logic computes the predicted cell densities at the plurality of time intervals.

According to embodiments, the system comprises at least the first and a second tank. The first tank is adapted to enable a user to transfer the culture medium in the first tank and the eukaryotic cells contained therein from the first tank to a second tank. For example, the first tank may comprise an opening or a pipe for manually or automatically transferring the medium with the cells from the first to the second tank.

The second tank being larger than the first tank and is adapted to receive the medium with the cells and additional cell free medium and to grow the transferred eukaryotic cells.

The control logic is configured to receive a further target cell density and a further target time, e.g. by reading the further target time from a storage medium or by receiving the target time via a GUI or a network interface from a user. The further target cell density represents a desired cell density of the eukaryotic cells at the further target time. The further target time represents a future point in time (later than the time of transferring the cells from the first to the second tank).

A cell density meter of the second tank is configured to measure the cell density of the eukaryotic cells in the culture medium of the second tank for each of a plurality of time intervals referred herein as "further time intervals" or "further prediction time intervals". The control logic is configured, for each of the further time intervals, for:

- computing a further predicted cell density at the further target time as a function of at least said measured cell density;
- comparing the further predicted cell density and the further target cell density;
- adjusting the temperature of the culture medium in the second tank if the further predicted cell density deviates from the further target cell density. The adjustment comprises increasing the temperature by 0.1° C. to 1° C. if the further predicted cell density is lower than the further target cell density; or decreasing the temperature by 0.1° C. to 1° C. if the further predicted cell density is higher than the further target cell density.

According to embodiments, the first tank is a bioreactor configured for growing the cell culture as batch-culture. The second tank is larger than the first tank and is a bioreactor configured for growing the cell culture as batch-culture. The first and second tanks are adapted for being used in a seed train cultivation process for generating a defined minimum number of cells for the inoculation of a production bioreactor.

According to embodiments, the second tank comprises a meter for measuring the cell density in the second tank and comprises a temperature control unit for adjusting the temperature of the medium in the second tank in accordance with a temperature control command of the control logic.

According to embodiments, the first tank is a bioreactor configured for growing the cell culture as a pre-production batch-culture. The second tank is larger than the first tank and is a bioreactor configured for growing the cell culture as a production culture.

According to embodiments, the eukaryotic cells are mammalian cells, in particular Chinese hamster ovary (CHO) cells.

According to embodiments, the culture medium in the first tank has a volume of 500 L or less.

According to embodiments, the control logic is configured for performing, for each of the plurality of time intervals:

- defining a current observation interval for the current time interval, the current observation interval having a predefined length and terminating at the end of the current time interval; and
- receiving all cell densities having been measured during the current observation interval.

The computing of the predicted cell density as a function of at least the measured cell density comprises extrapolating the cell densities measured during the current observation interval until the target time.

According to embodiments, the extrapolation comprises performing a curve fitting operation or a regression analysis on the cell densities measured during the current observation time.

According to embodiments, the time intervals are of equal length.

According to embodiments, the time intervals are of different length. In particular, at least some time intervals in the last third of the cell culture project are shorter than the time intervals in the first third of the cell culture project.

According to some embodiments, the control logic is configured for determining if the current time is close to the target time. In response to determining that the current time is close to the target time, the control logic reduces the length of all future ones of the plurality of time intervals.

According to embodiments, each of the plurality of time intervals has a duration in a range of less than 30 minutes, preferentially less than 10 minutes, e.g. a duration in a range of 1 to 10 minutes.

According to embodiments, the predefined length of the observation interval is in a range of 60 minutes to 480 minutes.

According to embodiments, the adjusting of the temperature comprises increasing the temperature by 0.1° C. to 0.5° C., preferentially by 0.1° C. to 0.2° C., or decreasing the temperature by 0.1° C. to 0.5° C., preferentially by 0.1° C. to 0.2° C.

According to embodiments, the control logic is configured to perform the temperature adjustment of the first tank only in case at least an adjustment time interval has lapsed since the control logic's previous temperature adjustment of said first tank. The duration of the adjustment time interval is in a range of 60-120 minutes.

According to embodiments, the control logic is configured to enable a human user (e.g. by providing a GUI) to enter the desired cell density and a future time when said desired cell density shall be reached via an interface of the control logic. The desired cell density represents a desired cell density of the eukaryotic cells at the entered future time. The control logic is further configured for controlling the growth of eukaryotic cells according to any one of the embodiments described herein. The growth control is performed such that the entered desired cell density is used as the target cell density, the entered future time is used as the target time and such that the eukaryotic cells are provided at the target cell density at the target time.

A "tank" as used herein is a container for holding, transporting, or storing liquids. A tank can be, for example, a bioreactor, in particular a pre-production or production bioreactor, a vial, or a harvest or transport tank. For instance, a tank can be a container having an interior volume suitable for culturing a plurality of cells (e.g., recombinant mammalian cells) in a liquid culture medium under a controlled set of physical conditions that allow for the maintenance or proliferation of the cells. Nonlimiting examples of tanks are bioreactors (e.g., any of the exemplary bioreactors described herein or known in the art).

A "bioreactor" as used herein is a vessel in which a chemical process is carried out which involves organisms or biochemically active substances derived from such organisms. This process can be, for example, aerobic or anaerobic. A plurality of different bioreactor types exist which vary in shape (e.g. cylindrical or other), size (e.g., milliliters, liters to cubic meters) and material (stainless steel, glass, plastic, etc.). According to embodiments, the bioreactor is adapted for growing cells or tissue in cell cultures. Depending on the embodiment and/or on the mode of operation, a bioreactor may be a batch bioreactor, fed-batch bioreactor or continuous bioreactor (e.g. a continuous stirred-tank reactor model). An example of a continuous bioreactor is the chemostat.

A "control logic" as used herein is a piece of program logic, e.g. an application program or module, a computer chip or another piece of software, hardware or firmware or a combination thereof that is configured for receiving and processing one or more measurement values from a tank comprising a cell culture, for processing the measurement values and for sending one or more control commands to the tank or hardware modules operatively coupled to the tank for controlling the growth of the cell culture. For example, the control logic may be a program module that is part of or interoperates with a bioreactor monitoring and control software. The control logic can also be part of a laboratory information management system (LIMS).

A "measuring device" or "meter" being "operatively coupled" to a tank can be, for example, a measuring device that is permanently or temporarily located inside of the tank or coupled to the wall of the tank and is configured to measure one or more physical or chemical parameters of the tank or the cell culture or culture medium contained therein. The measurement can be performed in response to a command or automatically on a regular basis.

An "online-measurement" as used herein is a process of obtaining a measurement value being descriptive of state features of a tank or of a cell culture or culture medium contained therein, whereby the duration required for performing the measurement is shorter than the time during which said features significantly change. A significant change can be a change by more than a predefined threshold value. For example, a change by more than 5% may be considered as a significant change. The threshold may vary for different features. Online-measurements may allow controlling a bioreactor in real time. In particular, an "online-measurement" as used can be a measurement that is performed directly on the tank or the cell culture or cell culture medium contained herein directly, i.e., without taking a sample from the medium and measuring the sample.

An "offline-measurement" is a process of obtaining a measurement value being descriptive of state features of a tank or of a cell culture or a cell culture medium contained therein, whereby the duration required for performing the measurement is longer than the time during which said features can significantly change. A significant change can be a change by more than a predefined threshold value. A typical example for an offline-measurement is the automated, semi-automated or manual sampling of the medium e.g. for measuring a current cell density. Offline measurements are based on a discontinuous sampling process. As the bioreactor features may meanwhile have changed since the sample was taken, controlling the bioreactor based on offline-measurement data tends to be of low quality due to significant latency times between the moment of measurement and the moment of performing a respective control operation. A significant change can be a change by more than a predefined threshold value, for example 2% or any other percentage value, depending on the respective state feature.

To "increase or decrease a temperature by X ° C." means, for instance, that a temperature of an object is increased or decreased relative to a current temperature measured e.g. at the same time when the prediction of the cell density is performed. According to embodiments, the tank comprises an online-thermometer.

The process of "curve fitting" as used herein is the process of constructing a curve, or mathematical function, that has the best fit to a series of data points (here: measured cell densities) possibly subject to constraints. Curve fitting can involve either an exact fit to the data, or smoothing, in which a "smooth" function is constructed that approximately fits the data.

A "regression analysis" as used herein is a process, which focuses more on questions of statistical inference such as how much uncertainty is present in a curve that is fit to data observed with random errors. Fitted curves can optionally be displayed on a GUI. The fitted curves are used to infer values of a function where no data are available, and to summarize the relationships among two or more variables.

The term "regression analysis" as used herein refers to a statistical process for estimating the relationships among variables and for representing the relationship in a function, e.g. a linear or non-linear curve function. Most commonly, regression analysis estimates the conditional expectation of the dependent variable given the independent variables—that is, the average value of the dependent variable when the independent variables are fixed. For example, the currently measured cell density and a growth model, e.g. a linear or exponential growth model, may be used for estimating the relationship between future times and the predicted cell density. Many techniques for carrying out regression analysis have been developed. For instance, linear regression and ordinary least squares regression may be used. Performing a regression analysis can comprise estimation of continuous response variables, as opposed to the discrete response variables used in classification (metric regression).

The term "extrapolation" as used herein refers to the use of observed data or the use of a curve having been derived from observed data (e.g. by fitting or otherwise interpolating the observed data) for computing predicted data values extending beyond the range of the observed data. For example, the extrapolation can predict future data values by fitting a curve through observed data values obtained in a past time interval. The curve can be a linear or a non-linear curve. The range of observed data can be, for example, a time interval in the past during which cell densities have been measured in a particular tank. Said time interval is also referred herein as "observation interval". As the observation time interval is determined de novo for each prediction, it is also referred to as "current observation interval". The computation of the future curve sections is subject to a degree of uncertainty since it may reflect the method used to construct the curve as much as it reflects the observed data.

The eukaryotic cell can be, in particular, a cell derived from any human and non-human mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Additional examples of mammalian cells are known in the art.

The term "seed train process" as used herein is a multi-step method by which a starting number of cells (e.g., recombinant mammalian cells) in a first cell culture is expanded into an N-1 cell culture that contains a sufficient number of cells to inoculate a typical production bioreactor at an initial cell density of greater than $0.25 \times 10^6$ cells/m L. Accordingly, a seed train tank is a vessel or bioreactor adapted for being used in a seed train process. The purpose of a seed train is the generation of an adequate number of cells for the inoculation of a production bioreactor. From thawed volumes used for cell line maintenance the cell number has to be increased by running the cells through many cultivation systems which become larger with each passage (e.g. T-flasks, roller bottles or shake flasks, small scale bioreactor systems and subsequently larger bioreactors). Single-use systems may be applied and systems which are inoculated at a partly filled state and culture volume is increased afterwards by medium addition). Typically, a production bioreactor is inoculated out of the largest seed train scale. A seed train offers space for optimization, e.g. choice of optimal points in time for cell passaging from one scale into the larger one. According to some embodiments, the cells in each tank used in a seed train process are grown to the same cell density in a defined time as the target cell density of the production bioreactor. In each of the seed train tanks and the production tank, the growth control method according to embodiments described herein can be applied based on the same, shared target cell density (but typically with different target times depending on the process particularities of each seed train step. In other embodiments, different steps in the seed train process use different target cell densities.

A "batch culture" as used herein is a cell culture grown in a tank operated in batch mode. When a tank, e.g. a bioreactor, is operated in batch mode, the medium remains the same throughout the entire cultivation period. Thus, the culture medium is neither supplemented or replenished (as is the case for a fed-batch process), nor is it partially replaced (as is the case for a chemostat bioreactor). In a batch culture, the growth of the cell, defined as an increase in the number of cells in a batch culture, typically increases very strongly (exponential phase) after initial constancy (lag phase), then decreases gradually (transition phase/"stationary phase") and, if necessary, becomes negative (decay phase). The cause of the stagnation of growth in a batch culture is a depletion of the nutrient medium and the accumulation of toxic substances.

A "fed-batch culture" as used herein is a cell culture grown in a tank operated in fed-batch mode. The tank can be, in particular, a production tank including a plurality of cells in a liquid culture medium. In fed-batch mode, fresh liquid culture medium is added periodically or continuously added to the tank without substantial or significant removal of liquid culture medium from the tank during culturing. The fresh culture medium can be the same as the culture medium present in the tank at the start of the culturing. In some examples of fed-batch culturing, the fresh liquid culture medium is a concentrated form of the liquid culture medium present in the tank at the start of culturing.

A "graphical user interface (GUI)" as used herein is a type of user interface that allows users to interact with electronic devices, e.g. computers or smart phones through graphical icons and visual indicators. A GUI enables a user to control software and/or hardware based functions, e.g. a control logic or a hardware module of a tank (e.g. a thermostat) through direct manipulation of the graphical elements (e.g. icons, buttons, bars, text fields, etc.) of the GUI.

The term "culturing" or "cell culturing" means the maintenance or proliferation of a mammalian cell (e.g., a recombinant mammalian cell) under a controlled set of physical conditions. The term "culture of mammalian cells" or "cell culture" means a liquid culture medium containing a plurality of mammalian cells that is maintained or proliferated under a controlled set of physical conditions.

The term "liquid culture medium" or "culture medium" means a fluid that contains sufficient nutrients to allow a cell (e.g., a mammalian cell or bacteria) to grow or proliferate in vitro. For example, a liquid culture medium can contain: amino acids purines, pyrimidines, choline, inositol, thiamine, folic acid, biotin, calcium, niacinamide, pyridoxine, riboflavin, thymidine, cyanocobalamin, pyruvate, lipoic acid, magnesium, glucose, trace metals or metal salts and buffers. In some embodiments, a liquid culture medium can contain serum from a mammal. In some embodiments, a liquid culture medium can contain a mammalian growth hormone, and/or a mammalian growth factor. Alternatively, a culture medium can be a minimal medium (e.g., a medium containing only inorganic salts, a carbon source, and water). The medium can comprise serum derived from a mammal. The medium can be a chemically defined culture medium in which all of the chemical components are known.

According to embodiments, the cells are adapted to produce recombinant proteins or peptides, e.g. immunoglobulins, or other forms of bio-products. The term "recombinant" or "engineered" means a peptide or polypeptide that is not naturally encoded by an endogenous nucleic acid present within an organism (e.g., a mammal). Examples of engineered proteins include enzymes, fusion proteins, antibodies, antigen-binding proteins and other types of peptides or proteins which are used in the pharmaceutical industry or biomedical research.

According to embodiments, the control logic starts adjusting the temperature of the first tank in dependence on the comparison result after a predefined minimum cell density in the medium of the first tank was measured. The minimum cell density may be, for example, 100000 cells/mL. This may be beneficial as the prediction accuracy is lower for low cell density values than for high density values. Moreover, in particular at the beginning of a cell culture project, the temperature thus can remain at a temperature that is optimal for a fast growth rate, and the "fine tuning" of the growth rate can be postponed to later phases of a cell culture project to avoid unnecessary delays.

According to some embodiments, the control logic performs the temperature adjustment of a particular tank only in case at least an adjustment time interval has lapsed since the control logic's previous temperature adjustment of said tank.

According to some embodiments, the system enables a user to specify the adjustment interval before a cell culture project is started and optionally enables the user to dynamically modify the adjustment interval during runtime of the project. For example, the GUI can enable a user to specify also an "adjustment interval" in addition to the target time, target cell density and further optional control parameters.

An "adjustment interval" as used herein is the minimum time that must have been lapsed since a previously exerted temperature adjustment by the control logic until the control logic is enabled to re-adjust the temperature of the same tank. Preferentially, the adjustment interval has a duration in the range of approx. 60-120 min.

Using an adjustment interval in the above specified range may be beneficial as the adjustment interval prohibits the control logic from changing temperature too frequently. This could have a negative impact on the overall growth rate of the cells as the metabolism of the cells would very frequently have to adapt to different temperatures.

The term "production tank" as used herein refers to a large-scale tank, in particular a large scale bioreactor adapted for cultivating cells in stationary phase. Production tanks are typically used for producing and optionally harvesting the desired bio-product, e.g. a protein or peptide. The large scale tank has, for instance, an internal volume over 500 L, 1,000 L, 5,000 L, 10,000 L, 20,000 L, 50,000 L, or 100,000 L. For example, a production tank can be a perfusion bioreactor.

The term "perfusion bioreactor" as used herein a bioreactor having an interior volume for culturing a plurality of cells (e.g., recombinant mammalian cells) in a liquid culture medium, and having a means (e.g., an outlet, an inlet, a pump, or other such device) for periodically or continuously removing the liquid culture medium in the bioreactor and having a means (e.g., an outlet, an inlet, a pump, or other such device) for adding substantially the same volume of a replacement liquid culture medium to the bioreactor. The adding of the replacement liquid culture medium can performed at substantially the same time or shortly after the removing the liquid culture medium from the bioreactor. The means for removing the liquid culture medium from the bioreactor and the means for adding the replacement liquid culture medium can be a single device or system.

BRIEF DESCRIPTION OF THE DRAWINGS

In the following embodiments of the invention are explained in greater detail, by way of example only, making reference to the drawings in which:

DETAILED DESCRIPTION

Figure 1:
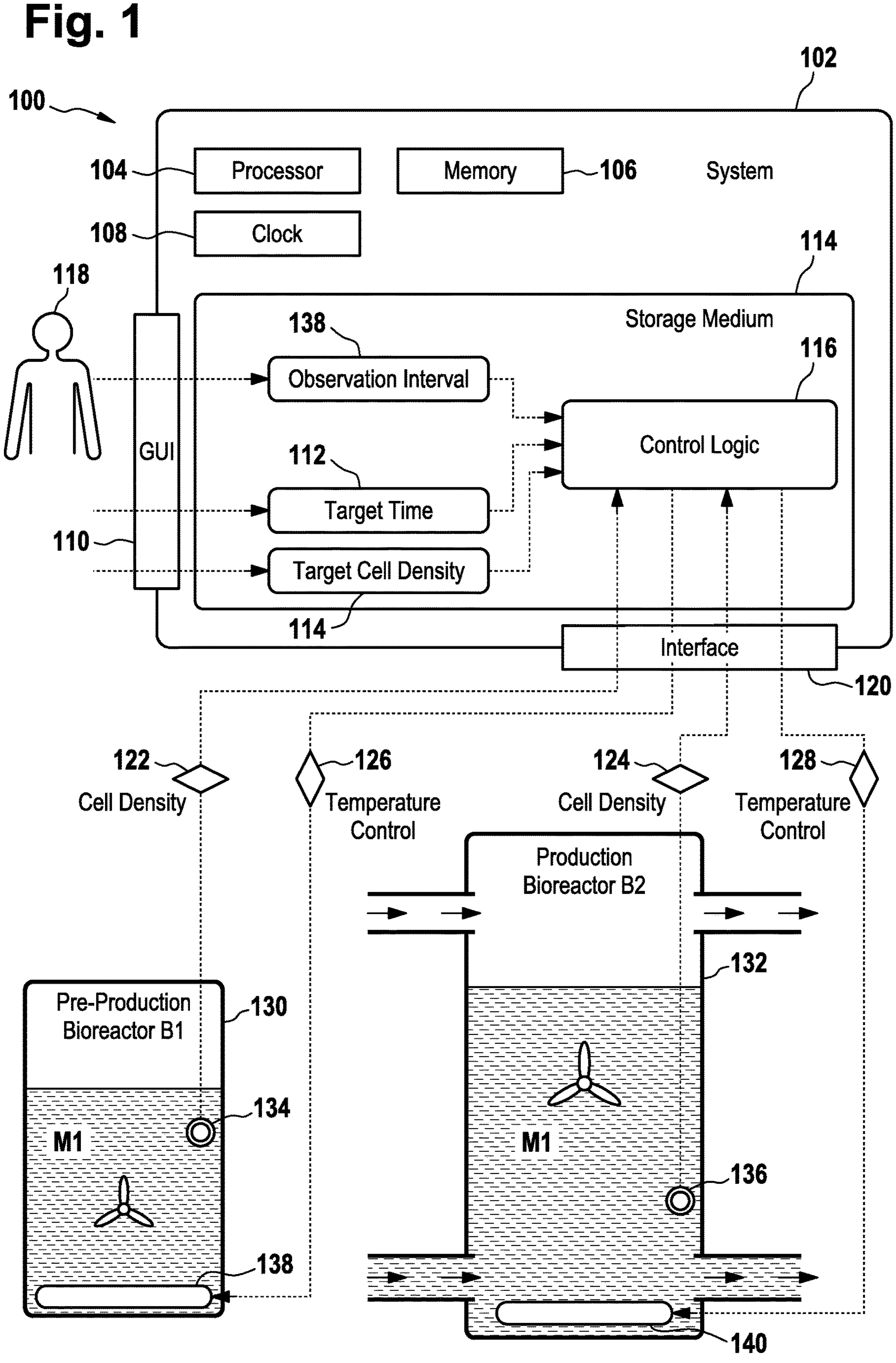
Figure 3:
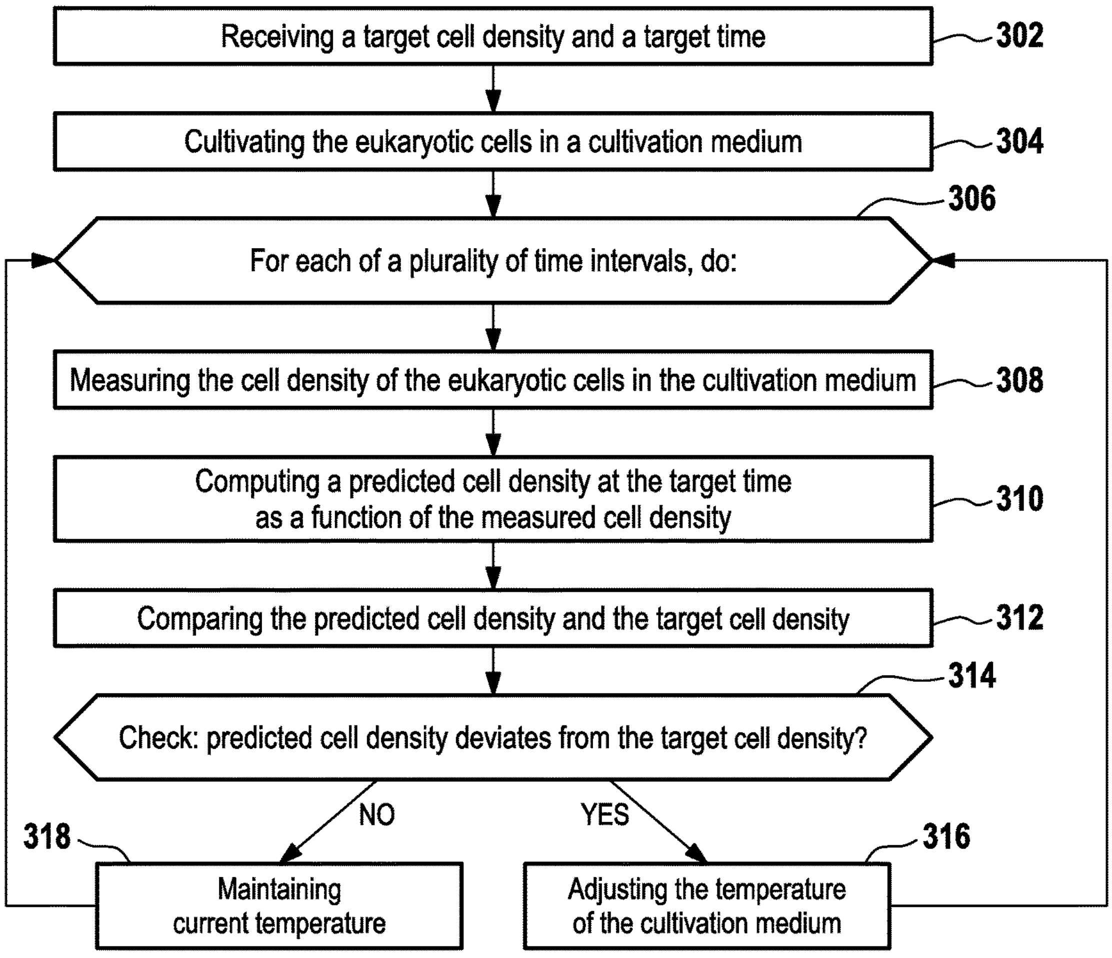
Figure 4:
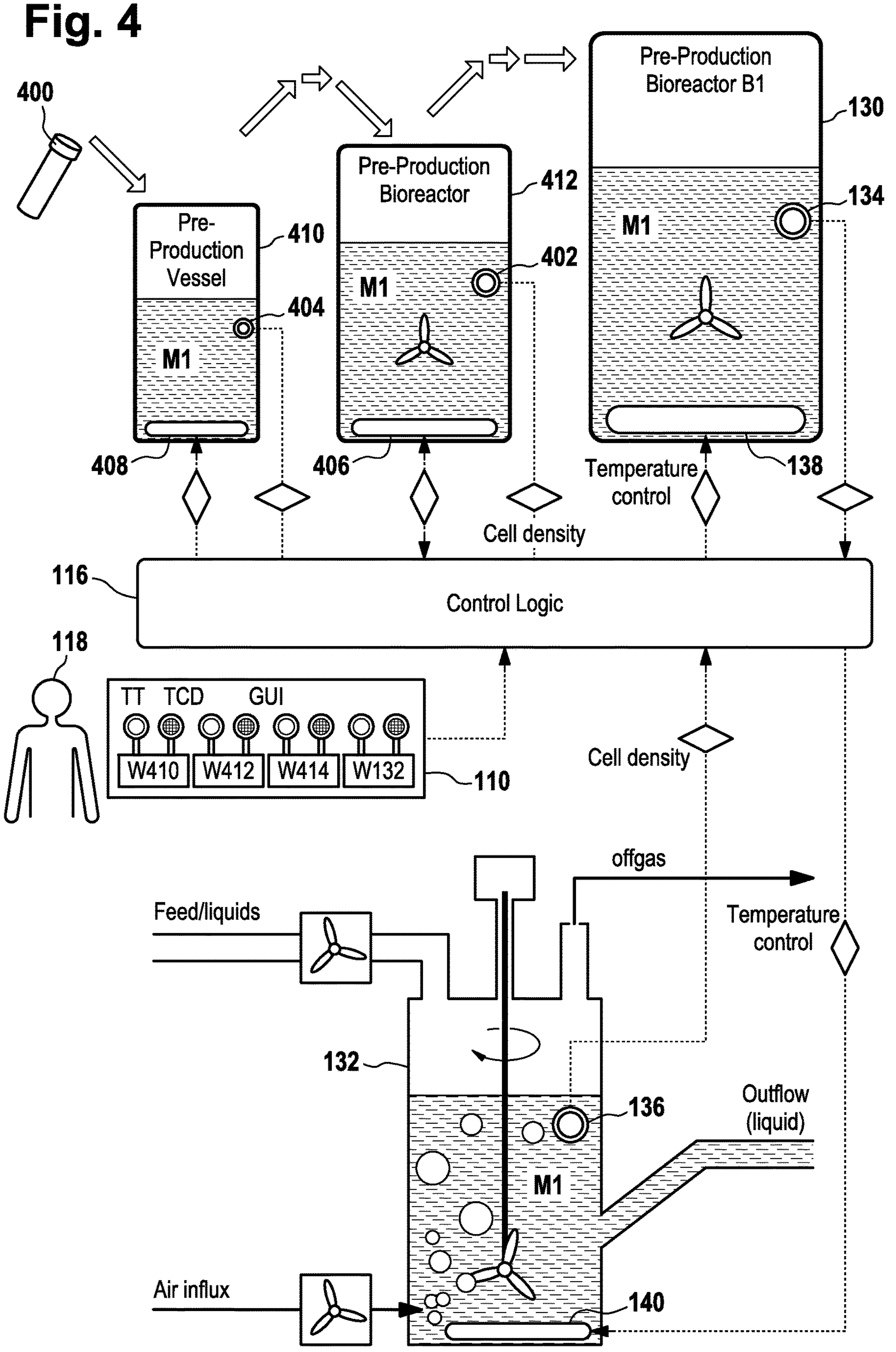
Figure 5:
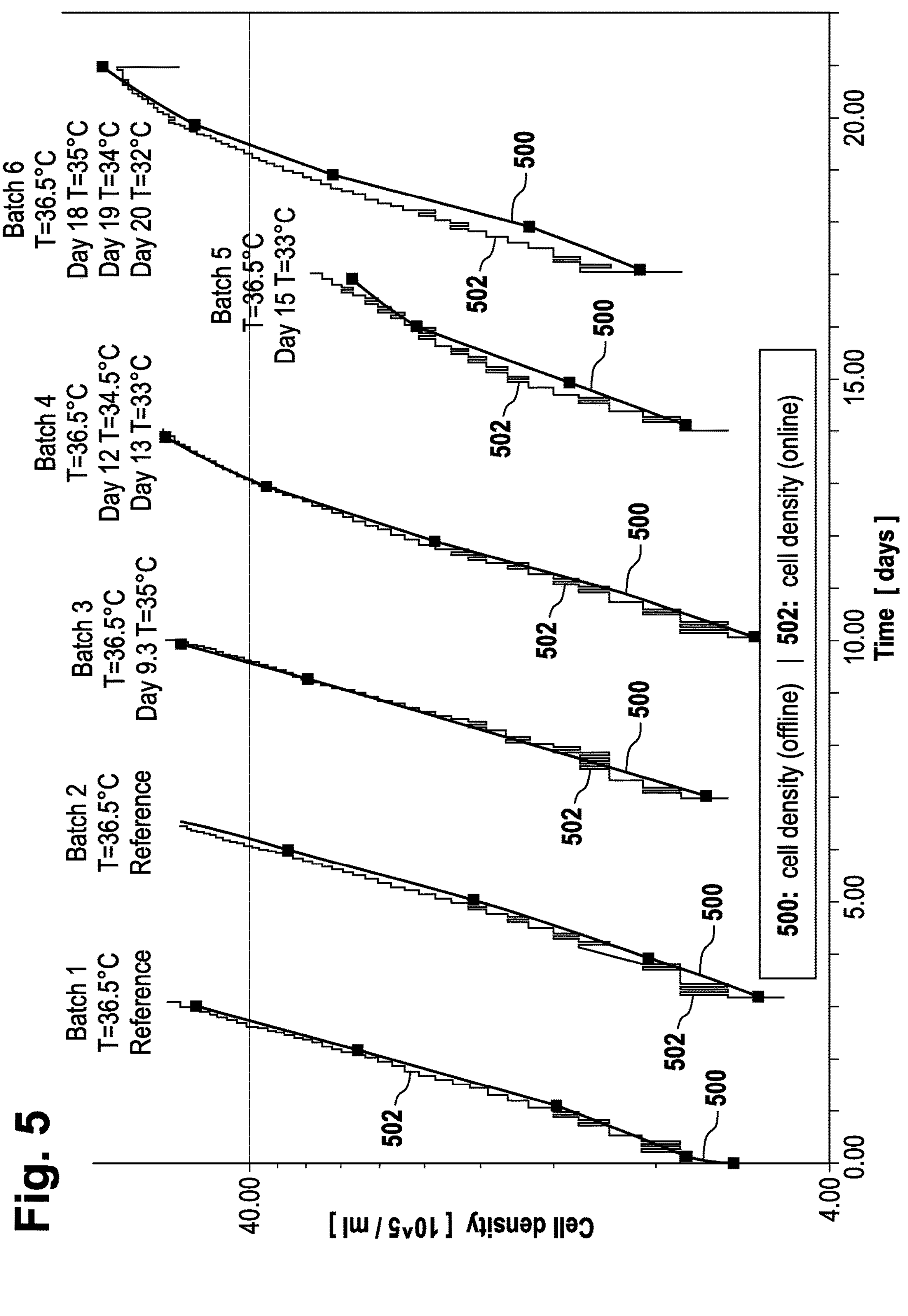
Figure 6:
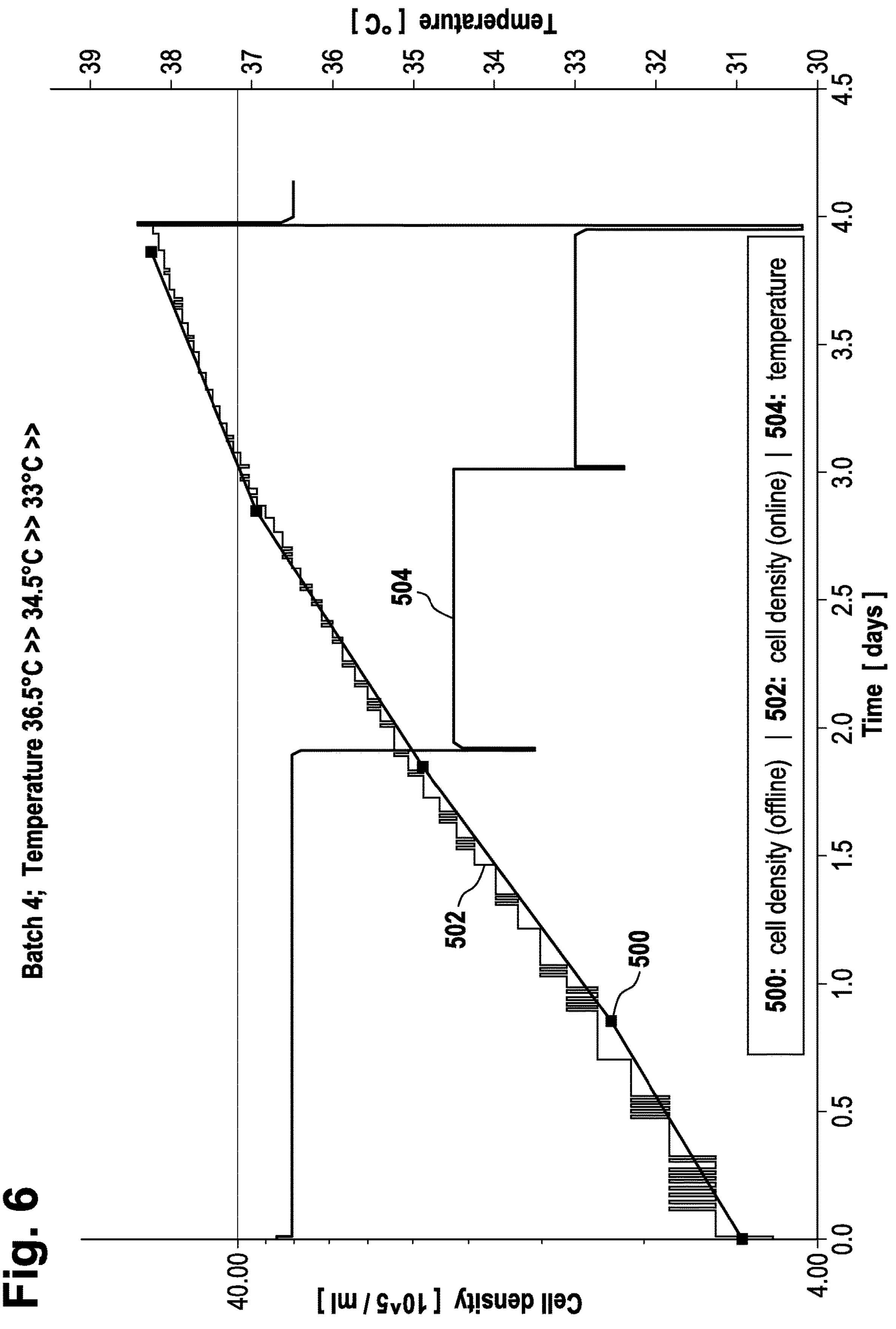
Figure 7:
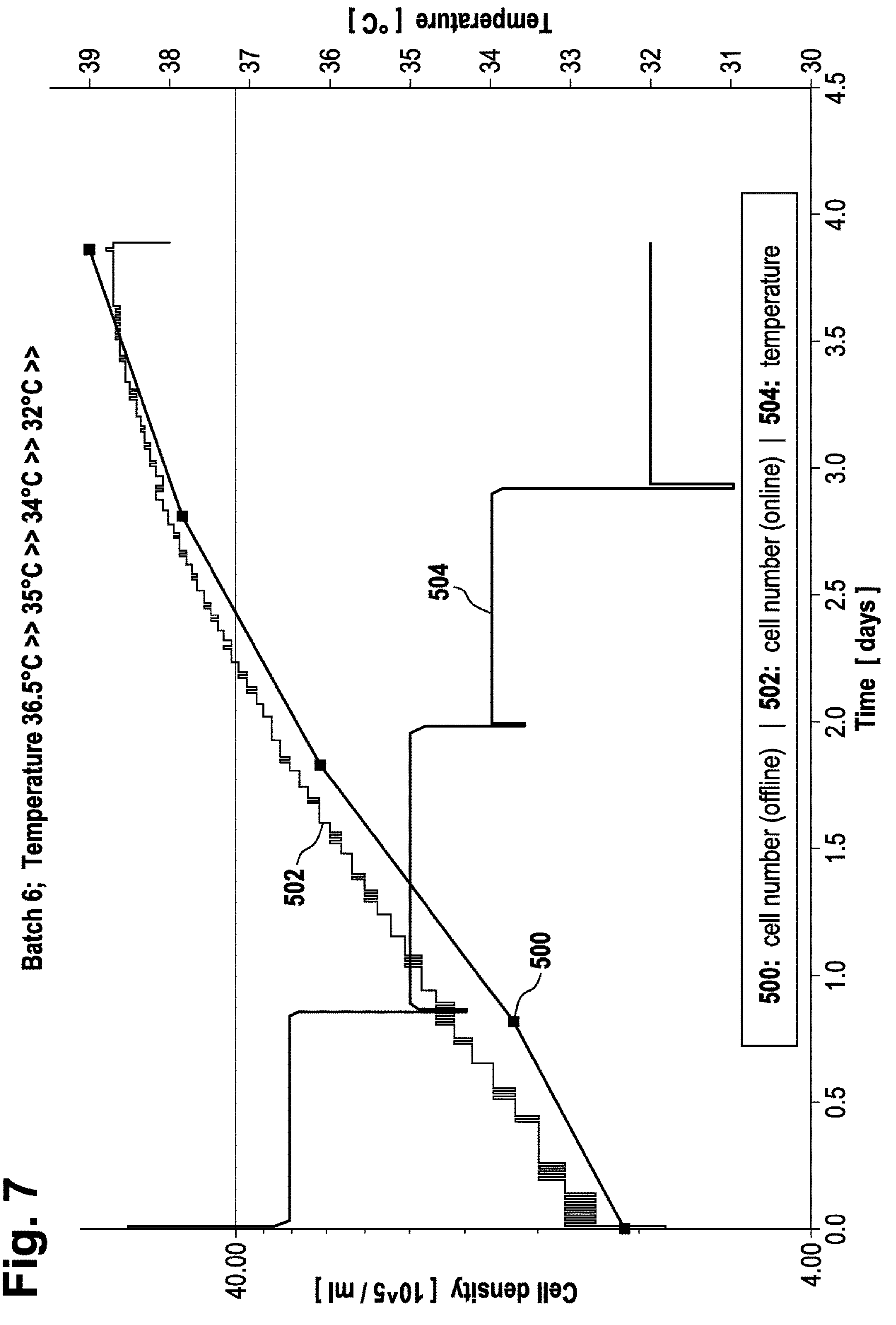
Figure 8:
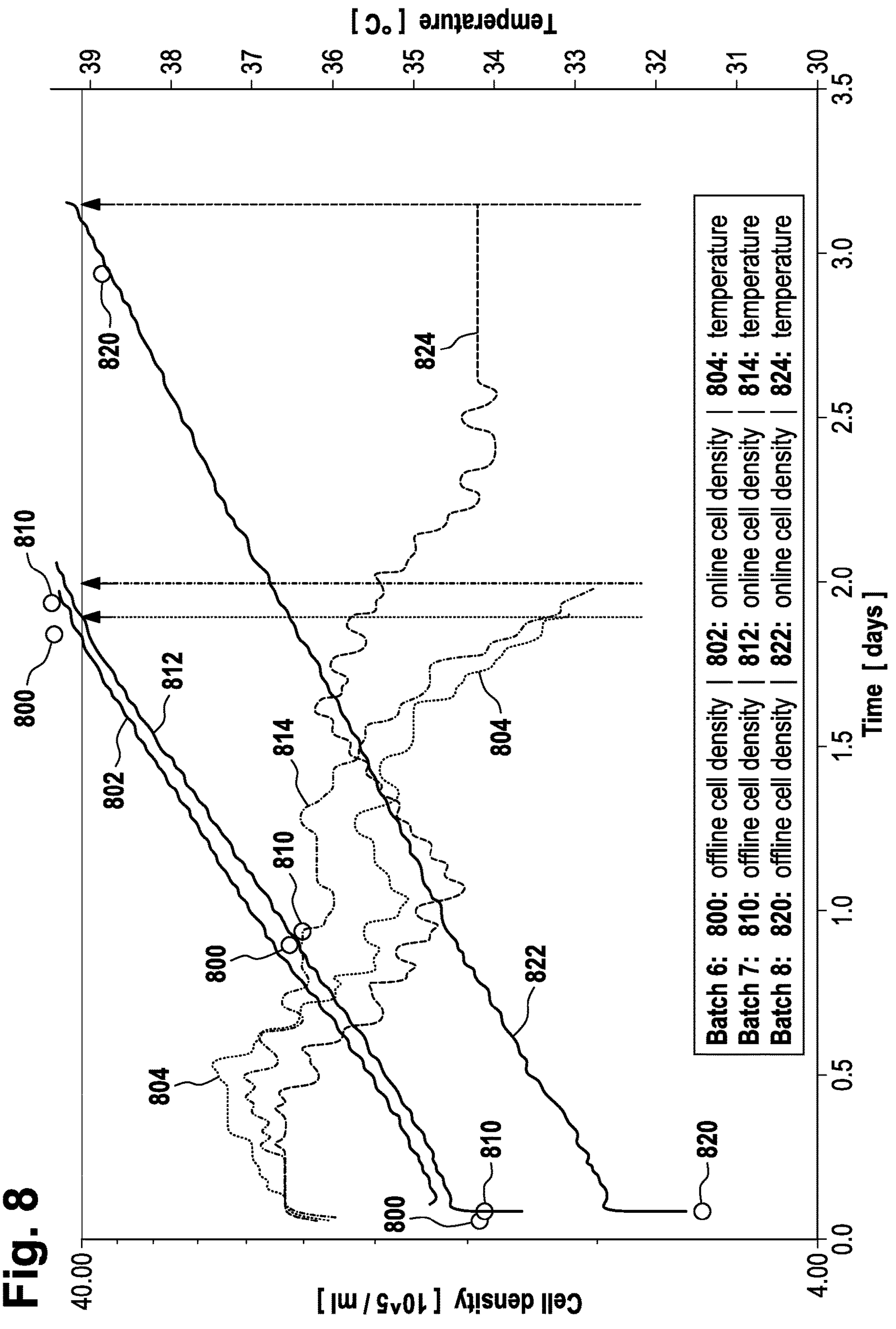
Figure 9:
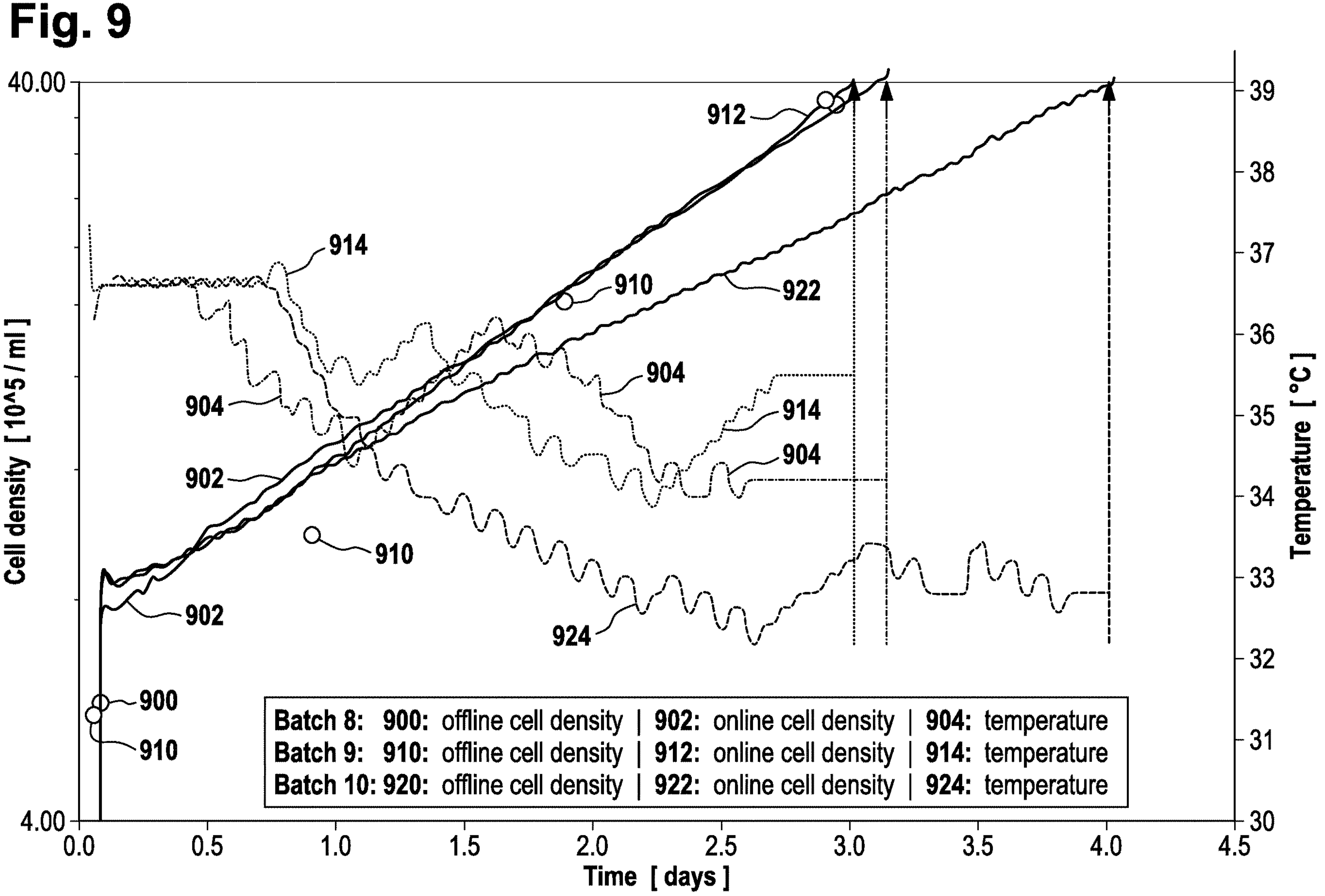
Figure 10:
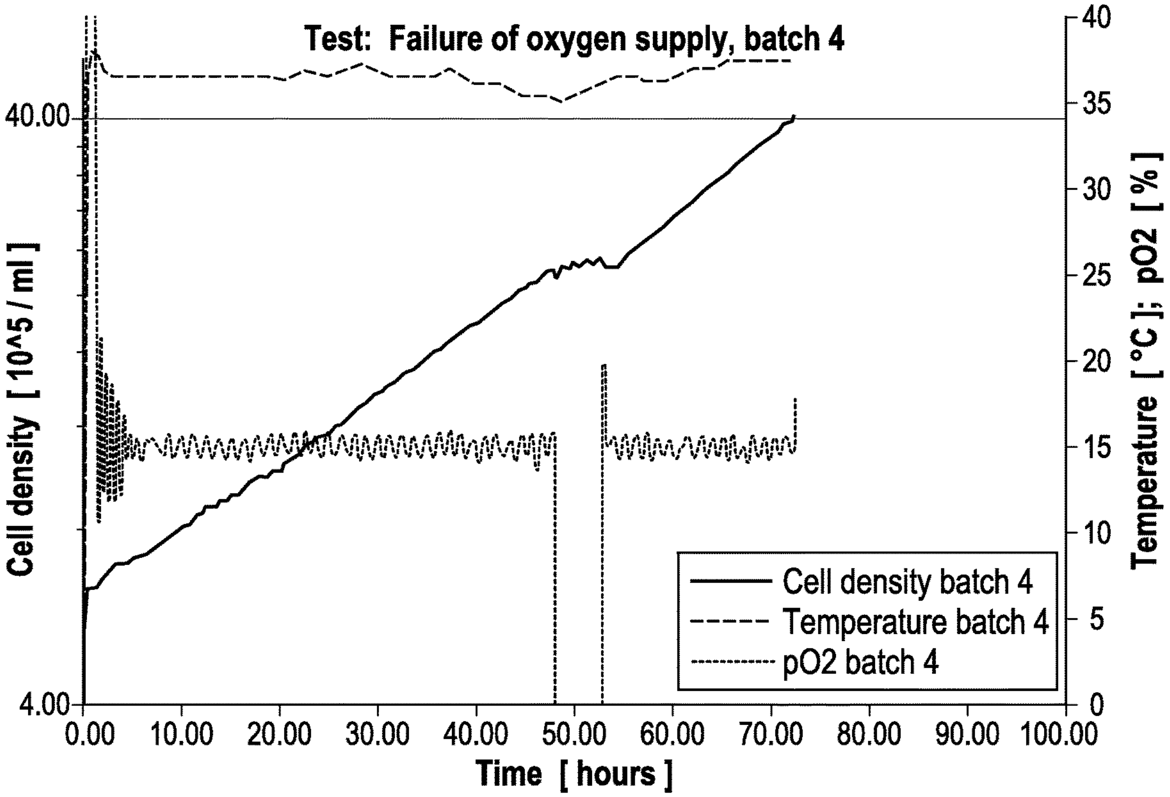
Figure 10:
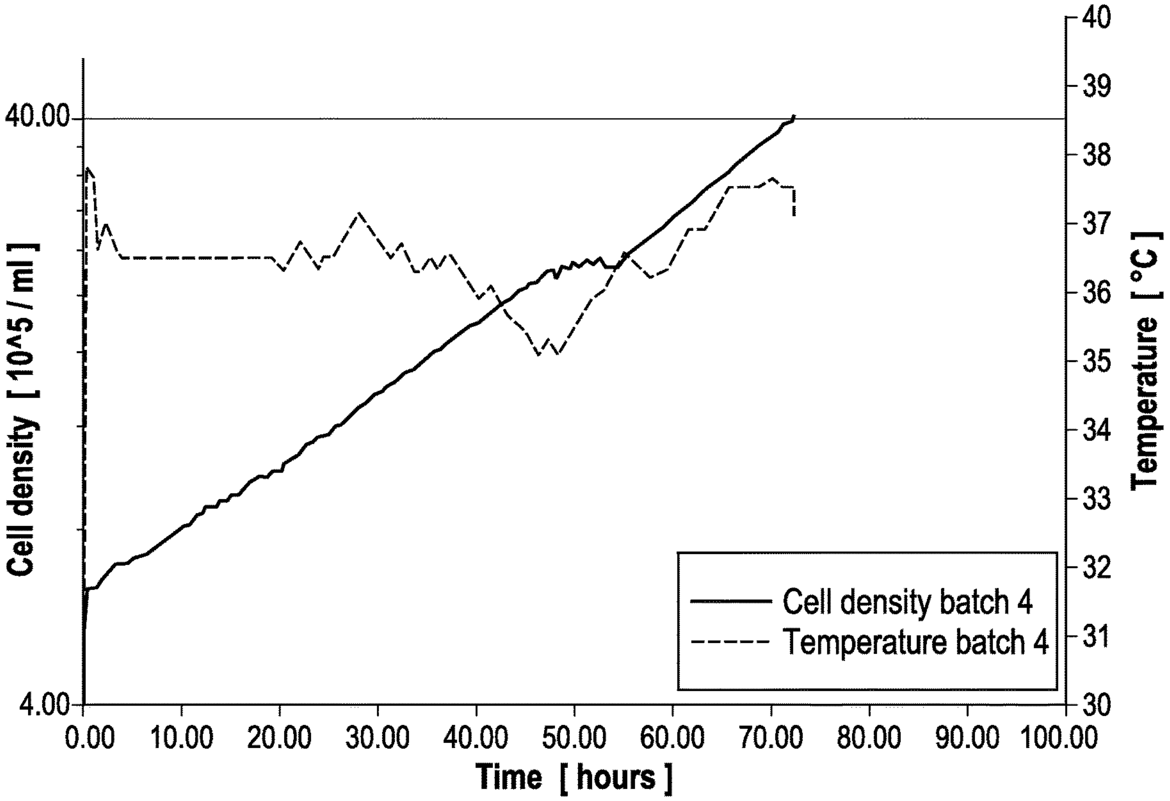
Figure 11:
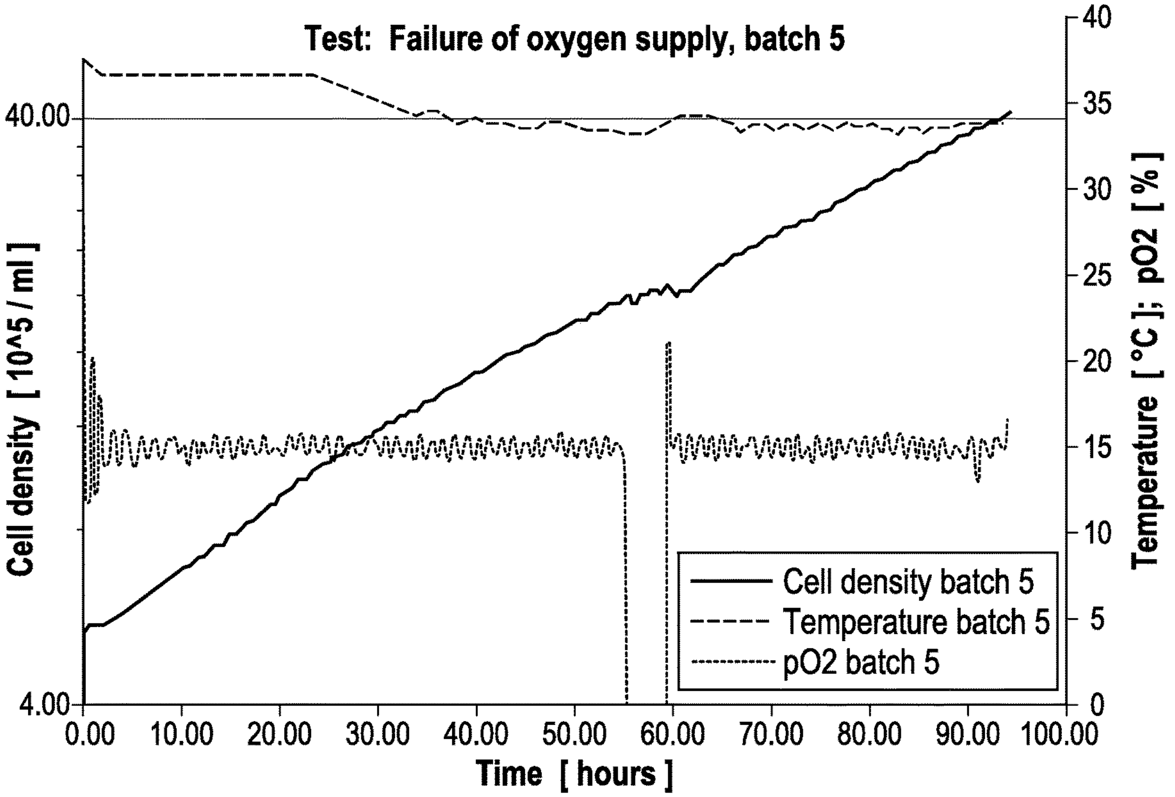
Figure 11:
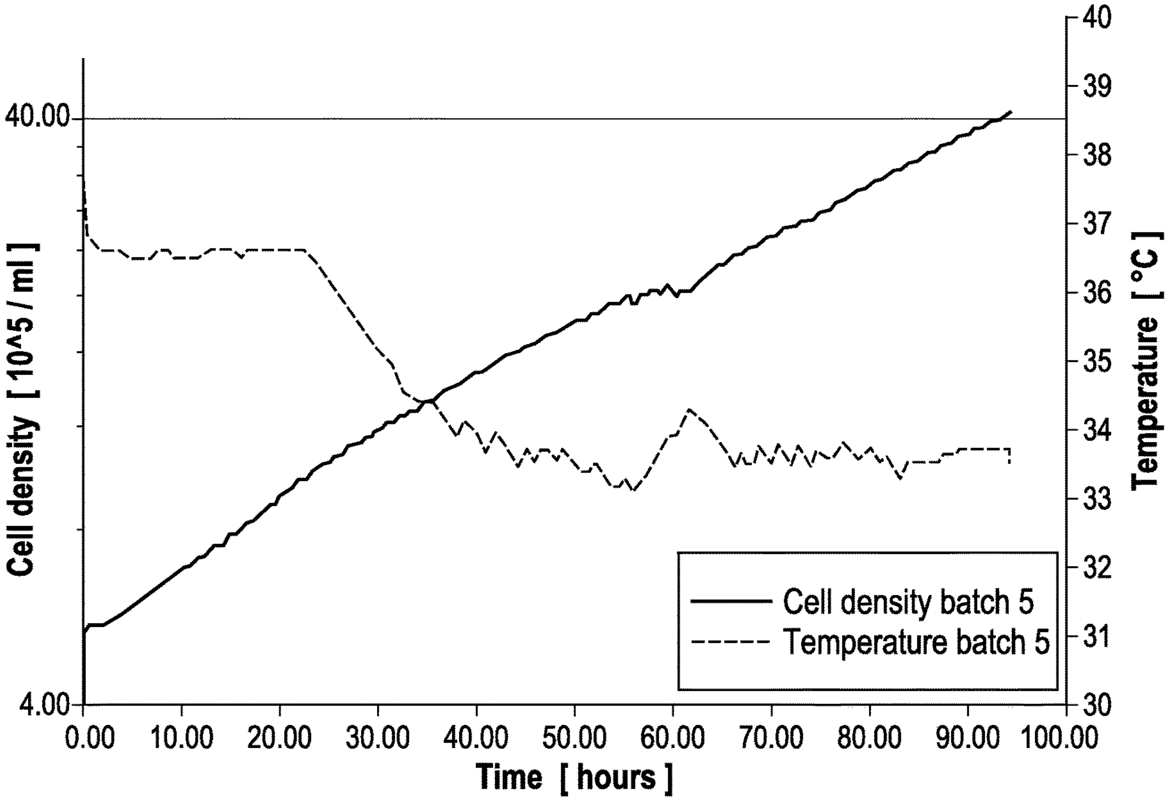
Figure 12:
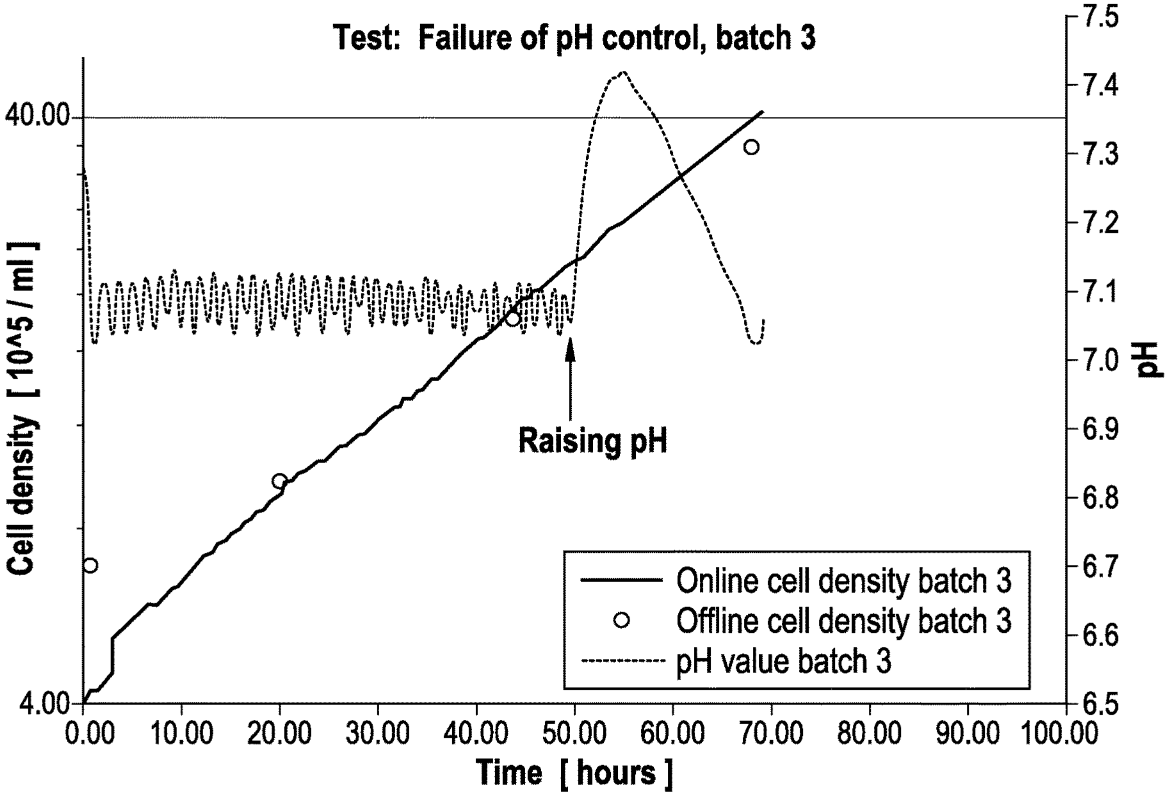
Figure 12:
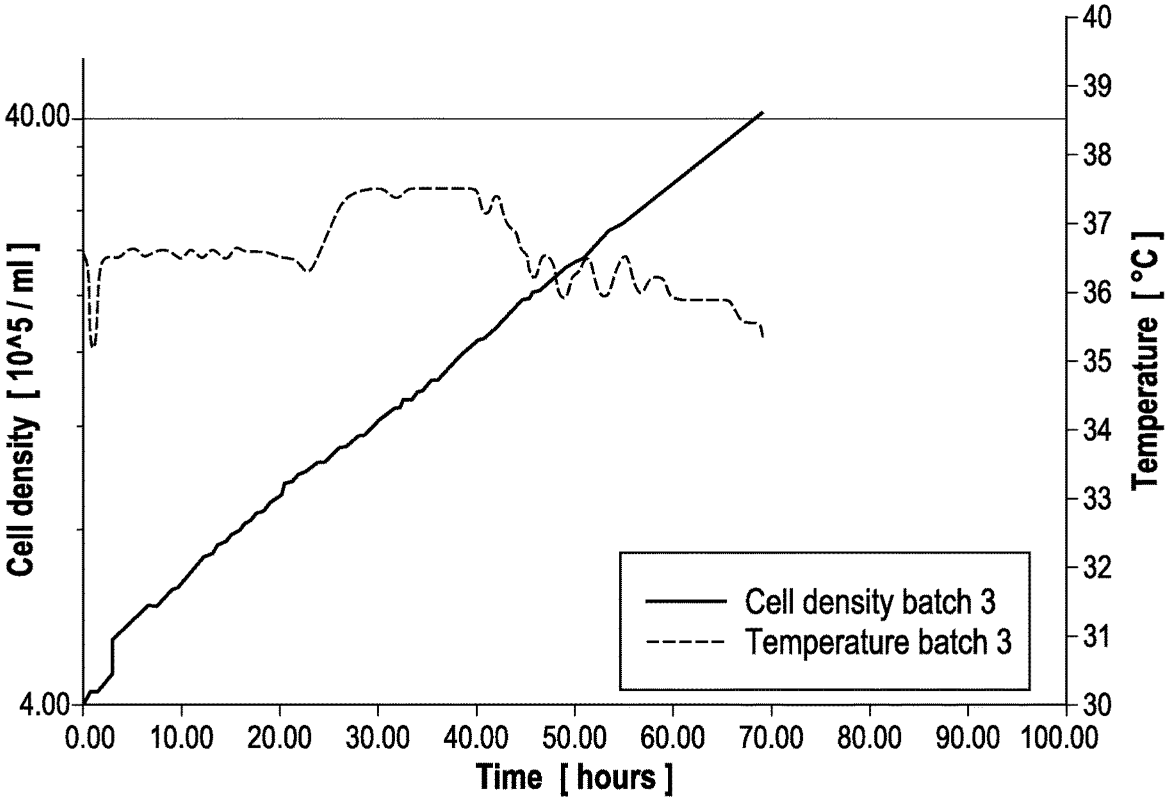
Figure 13:
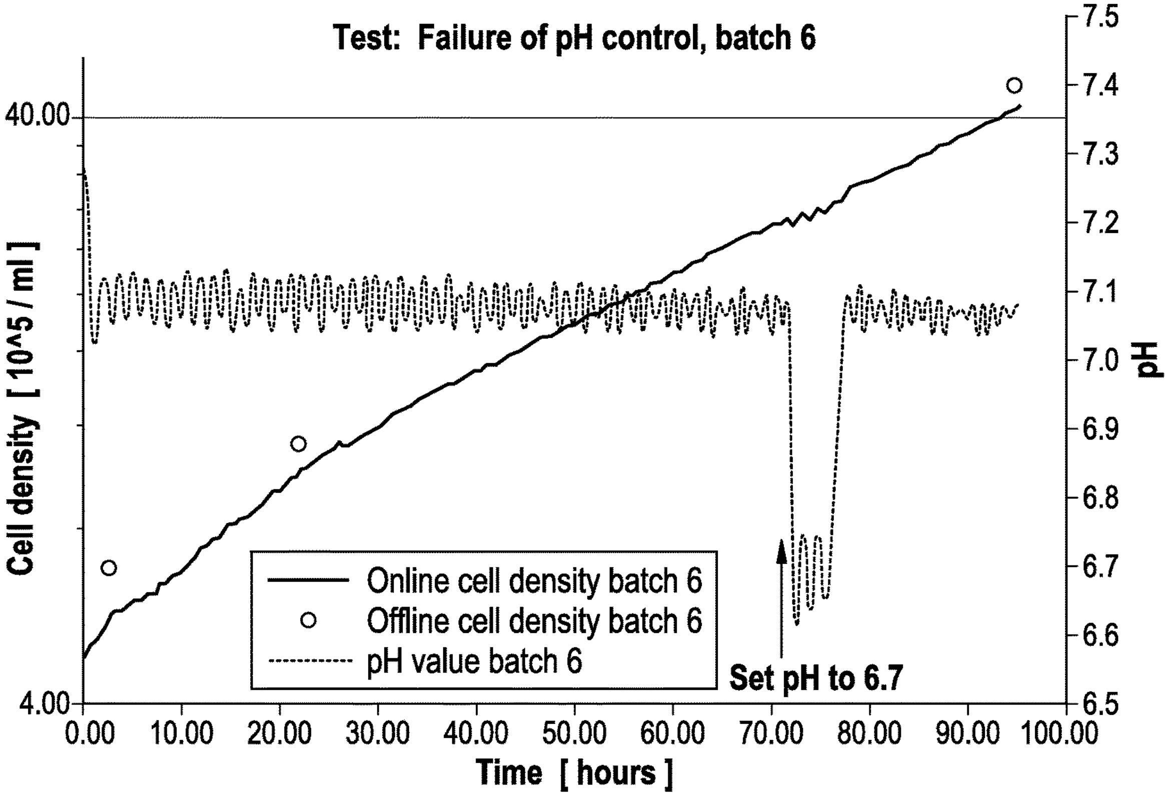
Figure 13:
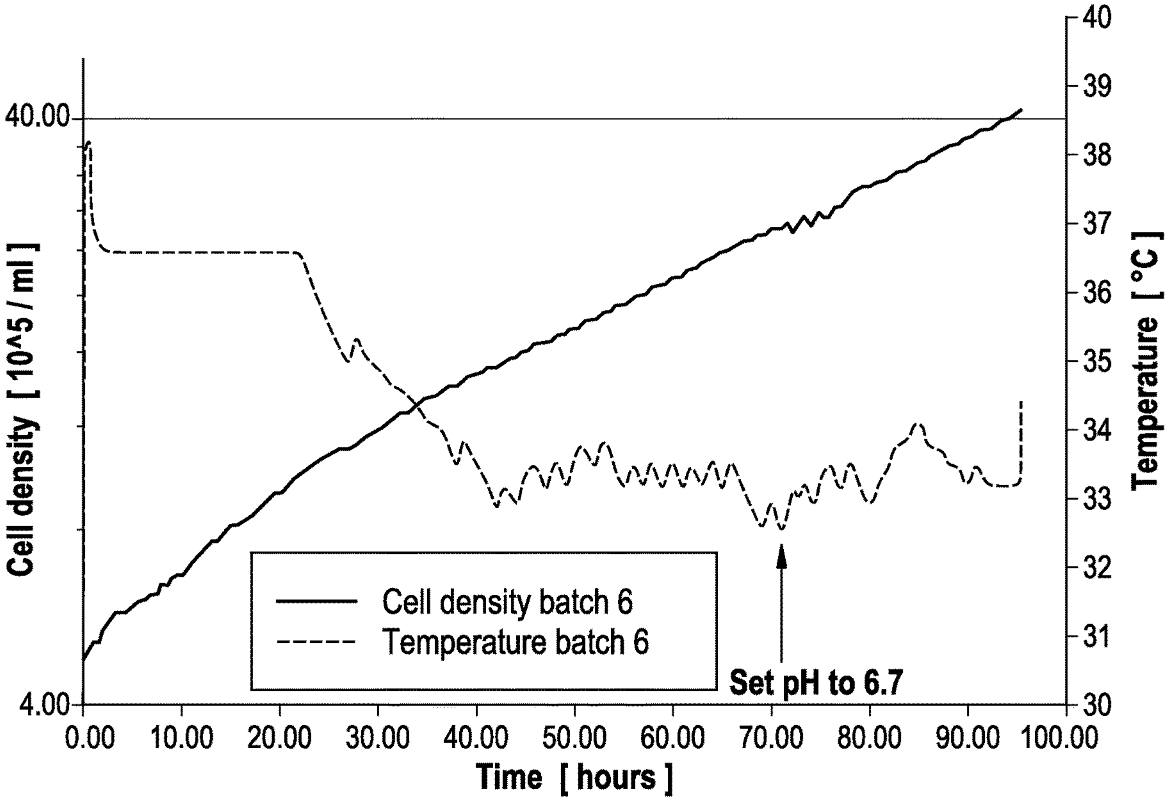
Figure 14A:
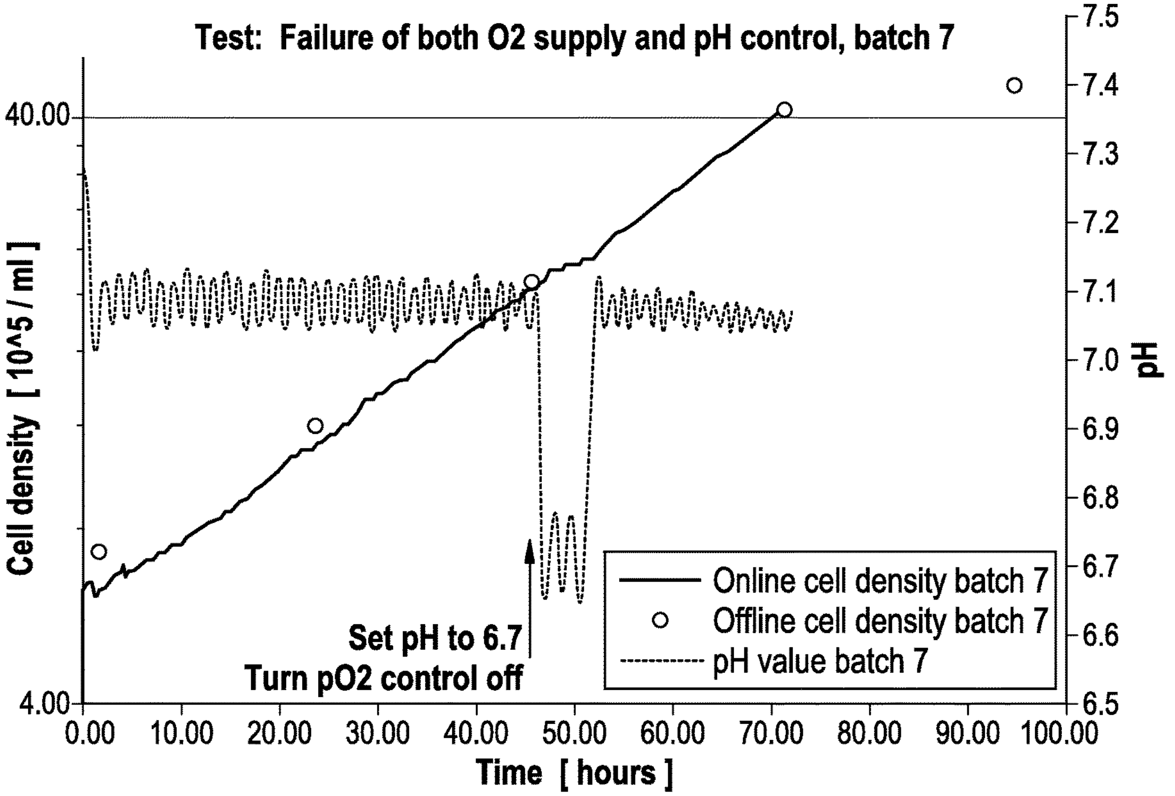
Figure 14A:
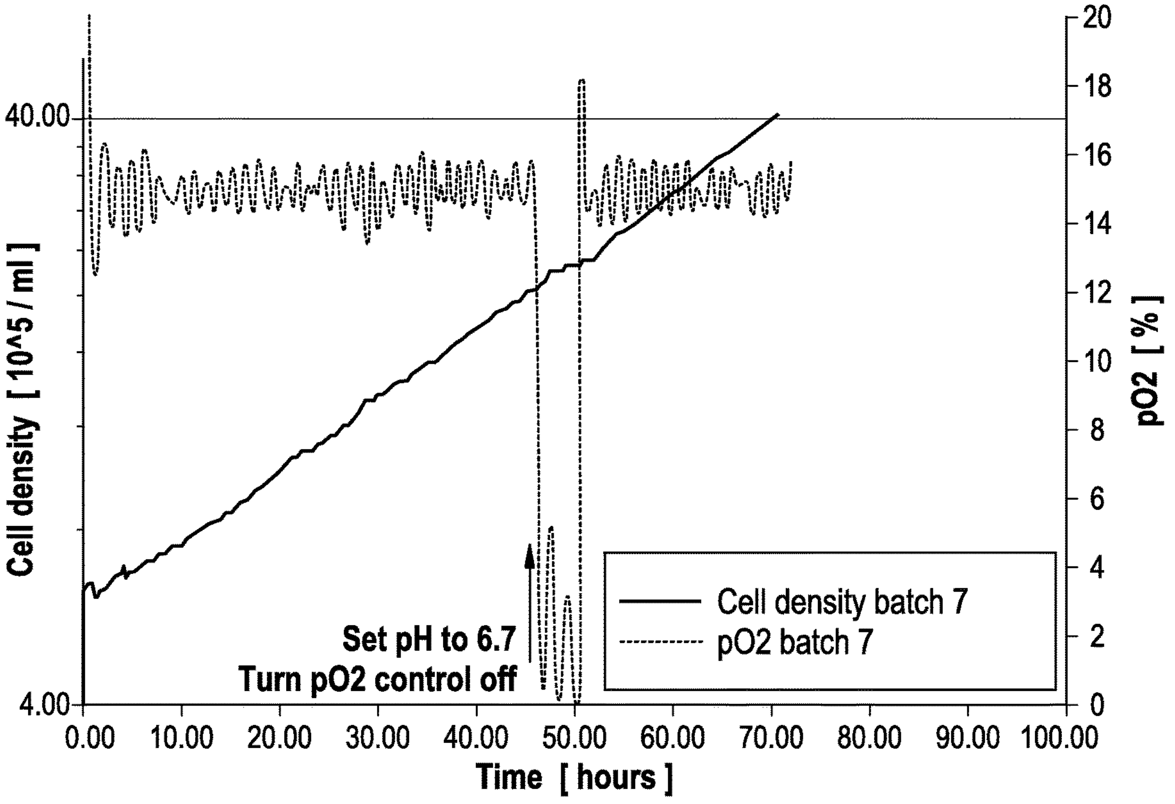
Figure 14B:
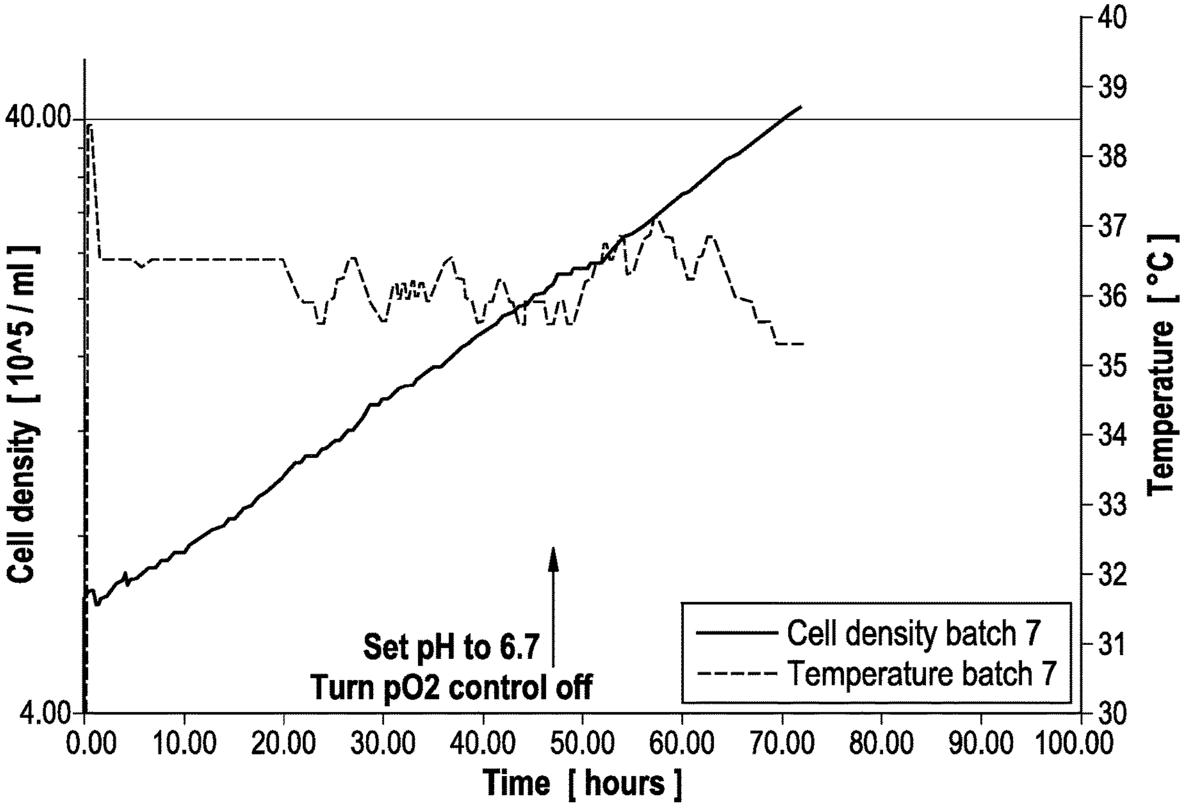
Figure 15:
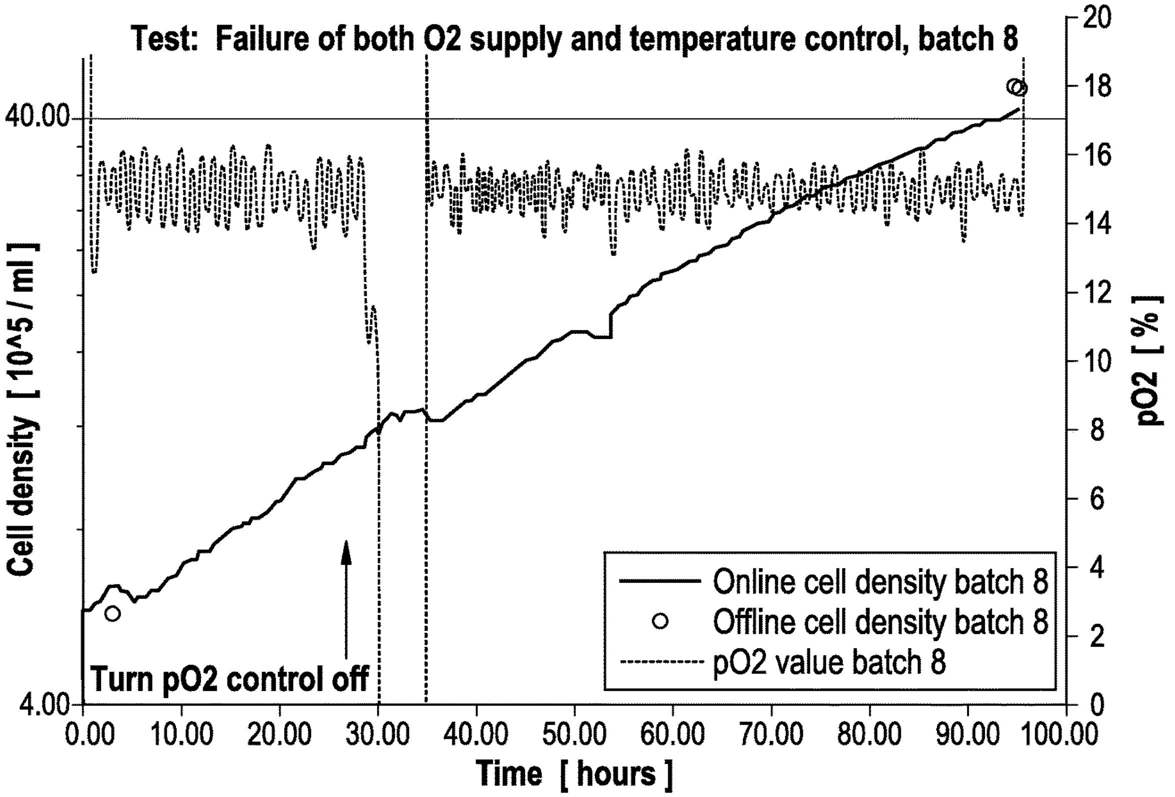
Figure 15:
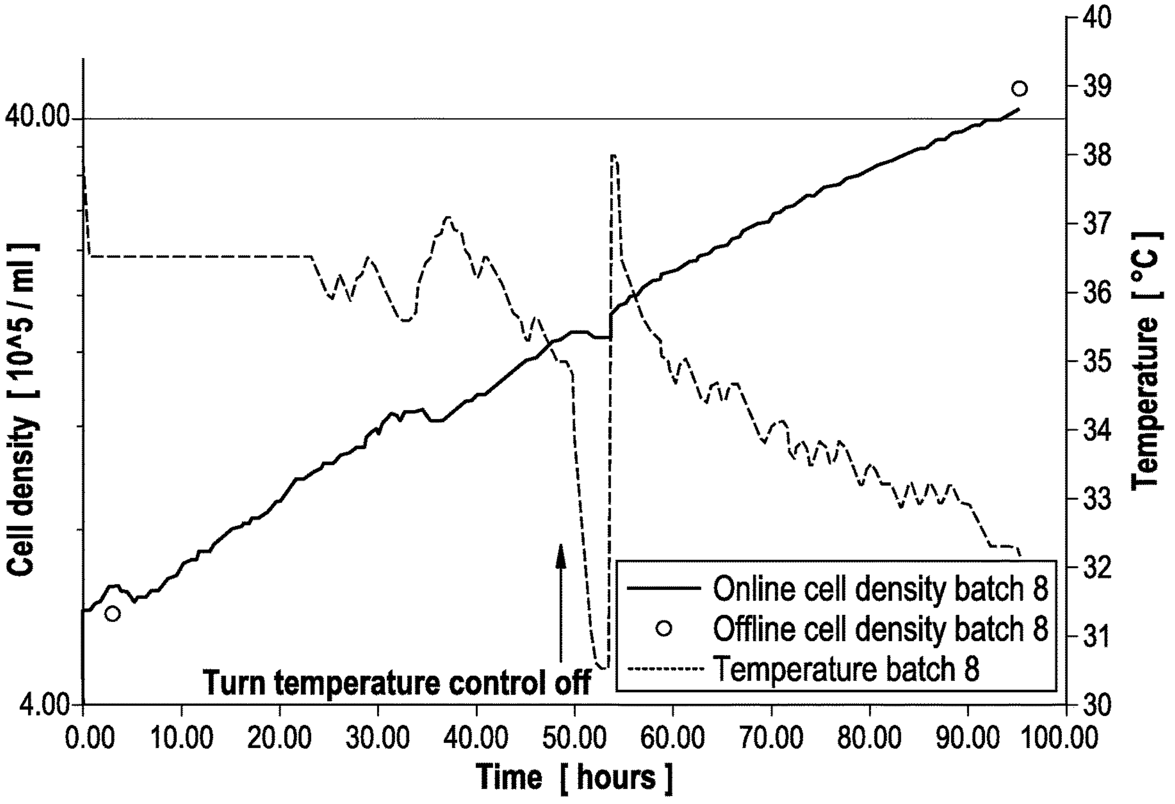

FIG. 1 is a block diagram of a system for controlling cell growth in a first and in a second tank;

FIGS. 2*a*-2*d* depict prediction time intervals and several different current observation intervals;

FIG. 3 is a flow chart of a method for controlling cell growth by adjusting the temperature;

FIG. 4 depicts a system comprising multiple pre-production tanks and a production tank;

FIG. 5 illustrates the cell density profiles of six cell culture projects;

FIG. 6 shows in greater detail the temperature effect on the cell density signal obtained for one of the 6 cell culture projects of FIG. 5;

FIG. 7 shows in greater detail the temperature effect on the cell density signal obtained for one of the 6 cell culture projects of FIG. 5;

FIG. 8 depicts a plot revealing the dependence of online and offline cell densities on temperature adjustments for three cell culture projects;

FIG. 9 depicts a further plot revealing the dependence of cell densities on temperature adjustments for further cell culture projects;

FIG. 10 depicts two plots illustrating the capability of the control logic to compensate for a failure of oxygen supply;

FIG. 11 depicts two plots illustrating the capability of the control logic to compensate for a failure of oxygen supply;

FIG. 12 depicts two plots illustrating the capability of the control logic to compensate for a failure of pH control;

FIG. 13 depicts two plots illustrating the capability of the control logic to compensate for a failure of pH control;

FIGS. 14*a* and 14*b* depict three plots illustrating the capability of the control logic to compensate for a failure of both oxygen supply and pH control;

FIG. 15 depicts two plots illustrating the capability of the control logic to compensate for a failure of both oxygen supply and temperature control.

FIG. 1 is a block diagram of a system 102 for controlling cell growth in a first 130 and in a second 132 tank. Growth control for each of the tanks can be performed in accordance with a method illustrated by the flow chart in FIG. 3. Thus, the system of FIG. 1 will in the following be described by making reference also to FIG. 3.

The data processing system 102 comprises one or more processors 104, a main memory 106 and a clock 108. The clock 108 is configured for determining the time in absolute or relative terms. It is used for determining prediction time intervals and observation intervals as depicted, for example, in FIGS. 2*a*-2*d*. In addition, the system 102 comprises a non-volatile storage medium 114 comprising computer readable instructions implementing a control logic 116. The control logic can be a standalone application program or a sub-module or unit of an application program or software framework used for controlling one or more bioreactors and/or lab devices.

In addition, the storage medium 114 comprises computer readable instructions implementing a graphical user interface GUI 110. The GUI enables a user 118 to specify and enter a target time 112 and a target cell density 114. Optionally, the GUI in addition enables the user to specify the duration of an observation interval 138 during which cell densities are measured and extrapolated for predicting the future time when a controlled cell culture reaches the target cell density 114. For example, the GUI 110 can be an HTML interface or a Java- or C#—based program logic. According to some embodiments, the GUI 110 enables a user not only to specify the target cell density, targets time and observation interval before starting a cell culture project, but also enables the user to modify the already entered and stored target cell density, targets time and/or observation interval during an ongoing cell culture project.

The system 102 further comprises an interface 120 for receiving measurement data from one or more tanks and/or for sending control commands to the one or more tanks. The interface forwards the received measurement data to the control logic 116 and forwards the control commands from the control logic to the one or more tanks.

The data processing system 102 can be implemented as a standard computer system, as a server computer system or as a mobile telecommunication device, e.g. a smart phone or tablet computer.

In the example depicted in FIG. 1, the system 102 is operatively coupled to and controls a pre-production bioreactor 130. The bioreactor 130 comprises an element 138 for increasing or decreasing the temperature of the medium. This element can be, for instance, a thermostat whose target temperature is controlled by the control logic 116. In addition, the pre-production bioreactor 130 comprises an online cell density meter 134 that is adapted to measure the current cell density in the medium M1 of the first bioreactor 130 without taking any samples. The bioreactor 130 comprises a culture medium M1 that is free of any cells when the pre-production cell culture project starts.

Before starting to grow cells in the pre-production bioreactor 130, the user 118 instantiates the GUI 110 and computer system 102 and enters a target cell density for a particular cell type and a target time defining the time when the cells in bioreactor 130 shall reach the target cell density. Typically, the target time is in the range of +/−20% of the time said particular cell culture project is known to enter a particular growth stage, e.g. the end of the growth stage for pre-production or production bioreactors or the end of the stationary phase for production reactors.

For example, the user may instantiate the GUI on Monday, 10.00 am. The user may want to grow a pre-production CHO cell culture that—according to the literature or previous experiments, typically requires 48 hours for reaching the desired cell density under “constant temperature” conditions of 37° C., one hour before starting a pre-production cell culture process in bioreactor 130 at 11.00 am by inoculating the bioreactor 130 with a thawed CHO cell sample. At 10.00 am, the user enters the target time 112, the target cell density and the observation time interval. For example, the user may enter 4 million cells per ml for the target cell density and “Monday, 11.00 am+48 hours” as the future target time. In addition, the user can set the prediction time intervals to e.g. about 1 minute and the observation interval e.g. to 90 minutes. The user may even set the target time to “Monday, 11.00 am+47 hours” for shortening the time required for performing the cell culture process by one hour.

At 11.00 am, after having configured the control logic via GUI 110, the user starts the pre-production cell culture by inoculating the cell-free medium M1 in the bioreactor 130 with a thawed CHO cell sample. The starting temperature of the tank can be 37° C.

In a first step 302 of the control method described herein, e.g. at about Monday 11.00 am, the control logic reads the target cell density 114, target time 112 and optionally the duration of the observation interval 138 having previously been entered by user 118 from storage medium 114. The read target cell density represents the desired cell density of the eukaryotic cells at the entered target time (Monday, 11.00 am+48 h). Of course, the time can be specified in various different formats, depending on the embodiment, e.g. as an absolute time or as a relative time starting from a current time or starting from a particular future time.

In step 304, the eukaryotic cells are cultivated in the culture medium M1 of the first tank 130. For example, step 304 can comprise inoculating the medium M1 in tank 130 with CHO cells. According to other embodiments, it is also possible that step 304 is performed immediately before step 302 are that both steps 302, 304 are basically performed in parallel.

The control logic may then automatically identify a series of "prediction time intervals", also referred to as "time intervals" $I_1, \ldots, I_{4367}$ of predefined length, e.g. one minute. The first time interval may start e.g. at, shortly before or shortly after the time of inoculation.

For each 306 of a plurality of time intervals (e.g. at the start or the end of each of the time intervals), the following sub-method is performed:

in step 308, the online cell density meter 134 measures the cell density 122 of the eukaryotic cells in the culture medium M1 in the first tank 130. The measurement value 122 is sent via interface 122 the control logic 116.

In response to receiving the measured cell density value 122, the control logic computes in step 310 a predicted cell density at the target time "Monday 11.00 am+48 h" as a function of at least the currently measured cell density. In particular, the cell density at the target time can be predicted as a function of the multiple cell densities having been measured during a sliding observation interval as depicted in FIG. 2.

In addition, the control logic compares in step 312 the predicted cell density and the target cell density.

In step 314, the control logic determines whether the predicted cell density is larger or smaller or identical to the target cell density. In case the control logic determines that the predicted cell density is identical to the target cell density entered by the user or is at least within a tolerance threshold band around the target cell density, the current temperature of the medium in the bioreactor 130 is actively or passively maintained in step 318. In case the control logic determines that the predicted cell density is lower than the target cell density entered by the user or is lower than a lower tolerance threshold below the target cell density, the control logic sends a temperature adjustment control command 126 to the thermostat 138 that causes the thermostat to increase the current temperature of the medium in the bioreactor 130 in step 316 by e.g. 0.4° C. Alternatively, in case the control logic determines that the predicted cell density is higher than the target cell density entered by the user or is higher than an upper tolerance threshold above the target cell density, the control logic sends a temperature adjustment control command 126 to the thermostat 138 that causes the thermostat to decrease the current temperature of the medium in the bioreactor 130 in step 316 by e.g. 0.4° C. According to embodiments, the GUI one 104 that enables the user 118 to specify the amount of temperature change imposed on the medium for each prediction time interval for which a temperature adjustment was considered necessary.

The sub-method comprising the steps 308-318 described above may be performed fully automatically for each of a plurality of time intervals of comparatively short range, typically one to several minutes.

According to some embodiments, the sub-method, e.g. step 314, may comprise a further check for determining if a termination criterion was fulfilled. For example, the control logic determines a termination criterion is fulfilled in case a predefined maximum number of prediction time intervals has lapsed, that the target cell density was reached, or that a predefined maximum duration for the cell culture project was exceeded, etc.

The above described method including the repeatedly performed sub-method 306-318 can be used for growing cells in a pre-production cell culture bioreactor 130 to a desired cell density that is appropriate for starting a succeeding cell culture project in a second tank 132, e.g. a production bioreactor. The production bioreactor also comprises a thermostat 140 controlled by the control logic via respective control commands 128 and an online cell density meter 136 that submits measured cell density values to the control logic 116. The measured cell densities and the temperature control commands 128 are communicated to and from the control logic via interface 120. The cell medium M1 in the second tank can basically be of identical composition as the medium in the first tank or can be of a different composition. The second cell culture project in the second tank is started by transferring the cells and optionally also the medium contained in the first tank after the target cell density was reached into the second tank. Additional, cell free medium is added to the second tank which results in a dilution of the transferred cells in the second tank.

Before the cells are grown in the second tank 132, the user 118 re-configures the target time 112 in accordance with the peculiarities of a production cell culture process in the second tank. For example, the first cell culture project may have terminated exactly at the target time, i.e. Monday 11.00 am+48 h", i.e., "Wednesday, 11.00 am". Transferring the cells from the first tank to the second tank, reconfiguring the control logic and supplementing additional media may require 30 minutes. A cell culture project for growing the cells in the target tank at 37° C. starting with the number of cells as provided by the first tank is known from the literature to require 74 hours. Thus, at Wednesday, 11.15, the user may re-configure the control logic by entering a new target time "Wednesday 11.30+74 h" or "Saturday 1.30 pm". After having transferred the cells from the first to the second tank, the second cell culture project is started at Wednesday 11.30 am, whereby the cell growth is controlled by adjusting the temperature of the medium in the second tank 132 as described above for the first cell culture project.

Figure 2A:
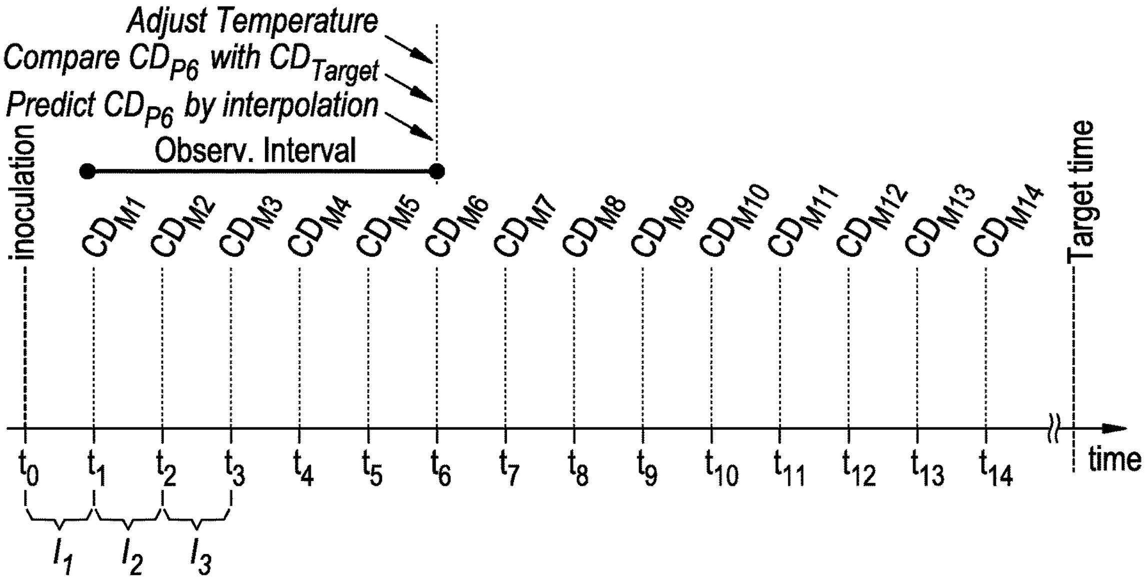

FIG. 2*a* depicts a plurality of "prediction time intervals" $I_1, \ldots, I_{4367}$, also referred to as "time intervals", which start when the cell culture medium is inoculated with the eukaryotic cells. For each time interval, e.g. at the end of each time interval, a current cell density in the medium in a controlled bioreactor is measured. For example, at the end of the first time interval $I_1$, cell density $CD_{M1}$ is measured. At the end of the second time interval $I_2$, cell density $CD_{M2}$ is measured. At the end of the third time interval $I_3$, cell density $CD_{M3}$ is measured. And so on. In addition, for each time interval or at least for time intervals that started after the laps of an observation interval, a predicted cell density $CD_P$ is computed by extrapolating cell density measurements obtained during a current observation interval.

For example, at the end of time interval $I_6$, a predicted cell density $CD_{P6}$ at the target time 112 is predicted by extrapolating the cell densities $CD_{M1}$, $CD_{M2}$, . . . , $CD_{M5}$, $CD_{M6}$ measured during the observation time interval. In addition, the control logic compares the predicted cell density $CD_{P6}$ with the target cell density 114 and adjusts, at the end of time interval $I_6$, the temperature of the controlled bioreactor in case the predicted cell density $CD_{P6}$ significantly differs from the target cell density 114.

Figure 2B:
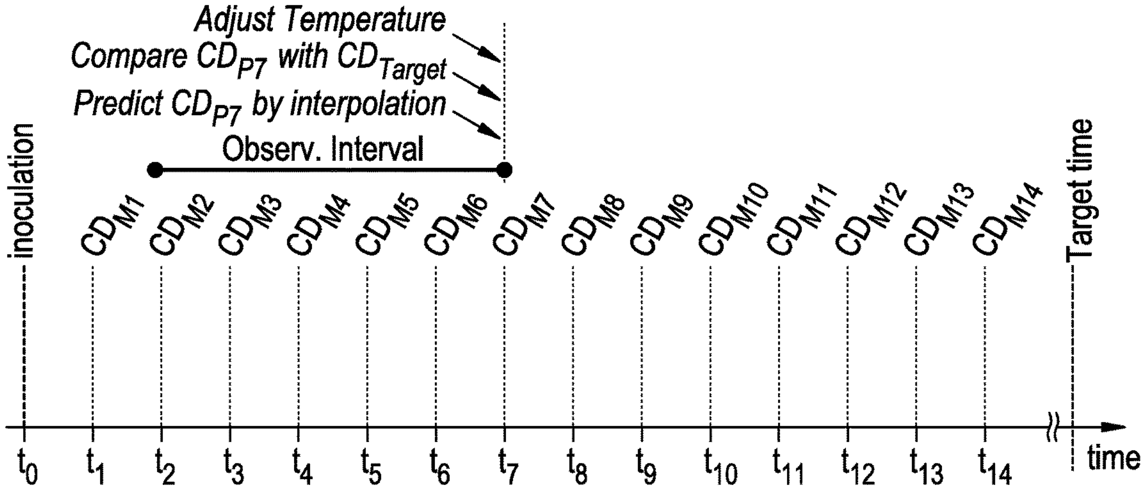

FIG. 2*b* illustrates the data processing steps performed by the control logic at the end of time interval $I_7$. The cell density $CD_{P7}$ at the target time 112 is predicted by extrapolating the cell densities $CD_{M2}$, $CD_{M3}$, . . . , $CD_{M6}$, $CD_{M7}$ measured during the observation time interval. In addition, the control logic compares the predicted cell density $CD_{P7}$ with the target cell density 114 and adjusts, at the end of time interval $I_7$, the temperature of the controlled bioreactor in case the predicted cell density $CD_{P7}$ significantly differs from the target cell density 114.

Figure 2C:
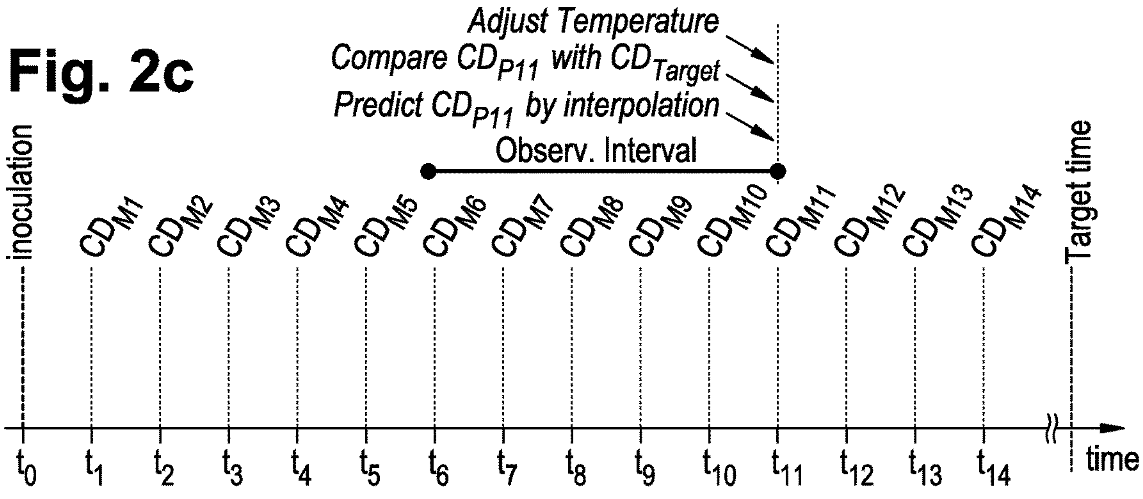

FIG. 2*c* illustrates the data processing steps performed by the control logic at the end of time interval $I_{11}$. The cell density $CD_{P11}$ at the target time 112 is predicted by extrapolating the cell densities $CD_{M6}$, $CD_{M7}$, . . . , $CD_{M10}$, $CD_{M11}$ measured during the observation time interval. In addition, the control logic compares the predicted cell density $CD_{P11}$ with the target cell density 114 and adjusts, at the end of time interval $I_{11}$, the temperature of the controlled bioreactor in case the predicted cell density $CD_{P11}$ significantly differs from the target cell density 114.

Figure 2D:
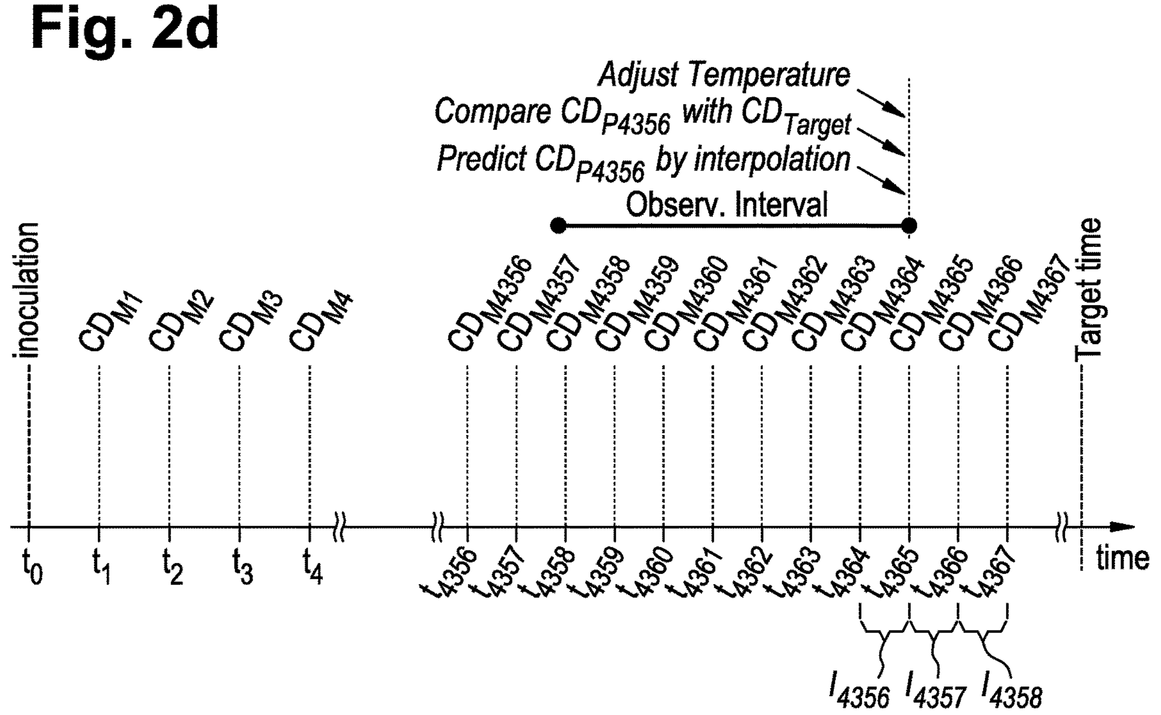

FIG. 2*d* illustrates the data processing steps performed by the control logic at the end of time interval $I_{4365}$. The cell density $CD_{P4365}$ at the target time 112 is predicted by extrapolating the cell densities $CD_{M4358}$, $CD_{M4365}$ measured during the observation time interval. In addition, the control logic compares the predicted cell density $CD_{P4365}$ with the target cell density 114 and adjusts, at the end of time interval $I_{4365}$, the temperature of the controlled bioreactor in case the predicted cell density $CD_{P4365}$ significantly differs from the target cell density 114. Compared to the time intervals depicted in FIGS. 2*a*-2*c*, the time intervals depicted in FIG. 2*d* are significantly shorter. For example, the time intervals depicted in 2*a*-2*c* can have a duration of several minutes, e.g. 15 minutes, and the time intervals depicted in the right portion of FIG. 2*d* may have a duration of a single minute. For example, the control logic may automatically use shorter time intervals upon determining that the current time is close to the target time, e.g. 2-3 hours ahead of the target time. This may be beneficial as the cell density is already high at this stage of the project and minor measurement errors may have a significant impact on the predicted target time. By using shorter time intervals, the number of predictions and the prediction accuracy may be increased as the robustness of the method against outlier measurements may be increased.

FIG. 4 depicts a system comprising multiple pre-production tanks 400, 412, 130 and a production tank 132. The pre-production tanks 400, 412, 130 are used in a seed train process for providing a sufficient number of cells to start a production cell culture project in the production bioreactor 132. The first pre-production bioreactor is inoculated with a thawed cell line sample 400 and a first pre-production cell culture is started in the first tank 410. Upon a first target cell concentration is reached in the first tank, the medium and the cells in the first tank are transferred to the second pre-production tank 412 and a second pre-production cell culture is started in the second tank 412. Upon a second target cell concentration is reached in the second tank, the medium and the cells in the second tank are transferred to the third pre-production tank 130 and a third pre-production cell culture is started in the third tank 130. Upon a third target cell concentration is reached in the third tank, the medium and the cells in the third tank are transferred to the production tank 132 and a production cell culture is started in the production tank 132. At least the production bioreactor can comprise a gas inflow line or pipe. For example, a single gas inflow line or pipe may be used for delivering environmental air or (already expanded) compressed air from special suppliers into the bioreactor. Said environmental air or compressed air may consist of a mixture of gasses, in particular N2, O2 and CO2 that is typical for the earth's atmosphere or has a different composition. In addition or alternatively, the single gas inflow line or pipe or any of the other gas inflow lines or pipes may be used for delivering individual gases such as N2, O2 and CO2 to the bioreactor. For instance, a bioreactor can comprise a microsparger for generating very finely dispersed gas bubbles from the inflowing gas for improving aeration of the cells in the tank.

Each of the tanks 410, 412, 130, 132 comprises a thermostat 138, 406, 408, 140 and an online cell density meter 134, 402, 404, 136 and is operatively coupled to and temperature-controlled by the control logic 116. The GUI 110 enables the user 118 to specify the target time and target cell density for each of the four cell culture projects individually. For example, the GUI may comprise a first window W410 for setting the target time and target cell density and optional further process parameters like interval length, observation interval length, amount of temperature adjustment per time interval etc. for the first tank 410. The GUI may comprise a second window W412 for setting the above parameter values for the second tank 412, a third window W414 for setting the above parameter values for the third tank 130 and a fourth window W132 for setting the above parameter values for the production tank 132.

FIG. 5 depicts six different batch cell culture projects which were performed for testing the impact of temperature adjustments on the growth rate of eukaryotic cells. In each of the cell culture projects described for FIGS. 5*ff*, a CHO cell line was grown in a 2 liters bioreactor B-DCU (Sartorius). The EVO200 system (Fogale, now Hamilton) was used for performing online cell density measurements. Cultivation of the cells of all batches was carried out in shake flasks according to reference cell culture protocols. The bioreactor used for each project was equipped with a pO2 electrode (Clark type) and a pH gel electrode. The working volume was always 1.3 liters and the bioreactor was aerated (headspace aeration and sparg rings). Across the head space, nitrogen enriched with carbon dioxide was constantly passed with 50 ccm to the bioreactor. Pure oxygen was introduced via the sparg ring in accordance with a pO2 regulator. The gas flows were adjusted via a mass flow controller (MFC). All online measurements were recorded via MFCS. The Fogale EVO200 system was used for online cell number determination. The permittivity (dielectric conductivity) of the culture was determined and converted by a constant factor into a cell density value. These values are referred to as the "online" cell densities. The measured values of the EVO200 system were read out via a specially programmed software and fed into a control logic configured for adapting the temperature of a bioreactor.

To check whether the permittivity based cell densities reflect the real cell densities correctly, they were occasionally compared with offline cell concentration having been determined by analyzing culture medium samples of the bioreactor. For the offline control of the cultures, samples were first taken at least once a day and the cell density was determined with a Cedex cell analyzer. In the later course of the project, the daily offline cell density determination was partly omitted. Although the permittivity is not constant over an entire fermentation process and is dependent on several parameters, it was nevertheless possible to work with only one conversion value in the relevant cell concentration range.

Two of the six batches were reference batches grown at constant temperature throughout the cell culture project. In the remaining four batches, the influence of the temperature on the cell growth was investigated by lowering the temperature during day intervals according to different schemes. Each of the two reference and the four test batch cultures always started at a standard temperature of 36.5° C. for about one day to adjust the cells to high growth rates. Thereafter, a temperature change was carried out in the four test batches 3-6 as indicated in the figures: batch 3 was grown for 9.3 days at 36.5° C. and afterwards at 35° C.; batch 4 was grown for 12 days at 36.5° C., then one day at 34.5° C. and the next day and all following days at 33° C.; batch 5 was grown for 15 days at 36.5° C. and then at 33° C.; batch 6 was grown for 18 days at 36.5° C., then one day at 35° C., then one day at 34° C. and the next day and all following days at 32° C.

For each of the batches, a continuous, smooth line 500 indicates the cell densities measured by converting permittivity measures by a single, empirically determined correction factor into a "measured cell density". The stepped curve 502 indicates the occasionally performed offline measurements for ensuring that the permittivity correctly reflects the real cell density over the whole temperature range tested. For performing the offline control measurements of the cell densities, samples were taken and the cell density was determined using a Cedex cell analyzer.

FIG. 5 shows that the cell growth rate can be controlled by temperature adjustments in existing bioreactor systems and that the permittivity measure accurately reflects the cell density over the relevant temperature range. The generated proteins and peptide examined so far did not show a deviation from the bio-products of the reference cell cultures although the temperature of the cell culture medium was modified during the cell culture process.

FIGS. 6 and 7 show in greater detail the temperature effect on the cell density signal obtained for two of the 6 cell culture projects. In both figures, a step wise decrease in temperature 504 resulted in a decrease of the growth rate, whereby the measured permittivity multiplied by a single constant conversion factor was a reliable measure of the cell density 502 (i.e., cell number in a given medium volume) as confirmed by occasional offline, sample-based cell density measurements 500.

In order to evaluate the influence of pH changes on the growth rate, additional cell culture projects ("batches") were performed (not shown). The additional batches revealed that no short-term influences of a modified pH in a wide pH range from pH 6.75 to pH 7.1 could be observed. The effect of pH changes appeared only with long latency times, if at all. Starting at a pH of 6.75 and switching to pH 6.8, an effect was observed after about 1.5 days, at pH 6.7 approximately one day and at pH 6.6 after half a day (see Batch 4). If the pH was decreased below 6.75, the culture needed to regenerate after renewed pH increase to standard values (6.9-7.1) a considerable time. Thus, it was observed that—contrary to temperature based growth control, a pH based growth control would be faced with the problems that in the physiological pH range, pH changes appear not to have a significant and immediate effect on cell growth and if a pH outside the physiological range is used, the cells need additional time to recover from the extreme pH values, thereby slowing down and reducing the flexibility of a cell culture project. It was observed that cell culture growth rates more strongly depend on temperature changes in the physiological temperature range of about 32-38° C. than on pH changes in the physiological pH-Range of about 6.8-7.2. Moreover, the cells recover from the non-physiological pH values significantly worse than from unusually low temperatures. Thus, pH adjustments were observed not to be suited to flexibly control cell culture growth rates.

Thus, according to embodiments, the temperature was used to provide automated control of cell culture projects as even small temperature changes had a significant, immediately reversible effect on the growth behavior.

According to embodiments, a control logic is configured to compute the current growth rate from the permittivity values determined by online (dielectric conductivity based) measurement devices (e.g. the EVO200) or via the biomass values (cell density values) calculated from the permittivity values by multiplying the permittivity factor with a conversion factor.

The conversion factor is determined in one or more reference cell culture projects by performing some offline cell density measurements in parallel to the permittivity measurements and identifying a conversion factor that, if multiplied with the permittivity value, returns the offline cell density.

According to embodiments, the time intervals for performing permittivity offline measurements and for predicting the cell density at the target time are 60 seconds. The permittivity values obtained for an interval are logarithmized by the control logic (base e) and stored temporarily or permanently in a storage medium. Optionally, offline cell densities are measured from time to time and stored in association with a respective online cell density. The logarithmized cell density values are subjected to a linear regression over a predetermined observation interval (e.g., 90 minutes). A new calculation is carried out after each new permittivity (and thus, online cell density) measurement value (for example after every 60 seconds). The slope of the regression line is then used to determine the growth rate p of the cells over the current observation interval. This value p fluctuates naturally for a few measured values, but is consolidated within the specified observation interval. The longer the observation interval, the more stable is the calculated growth rate and the more accurate the predicted cell density at the target time.

Using the calculated growth rate, a prediction of the prospective cell density at the target time is calculated and the predicted cell density is compared with the target cell density set by a user. The target time and target cell density is defined at the beginning of the batch process which may also be the time of starting the control logic. If the prognosis yields a cell density above the target cell density, the temperature is lowered by a small value (e.g., 0.4°); If the predicted cell density is below the target cell density, the temperature is slightly raised (e.g., 0.2°). After the temperature change, a new observation interval is started automatically and the cycle starts again. This is continued until the target time is reached or another termination criterion is fulfilled.

For instance, an externally controllable water bath (with counter-cooling) can be used for adjusting the temperature of a bioreactor. However, any control system can be used, which allows the transfer of external values (setpoints, control parameters) to an element that is able to increase and decrease the temperature of a medium in a tank.

FIG. 8 shows the online (e.g. permittivity based or online microscope based) cell densities 802, 812, 822, the occasionally measured offline cell density values (symbols) 800, 810, 820, and the temperature signal (dashed lines) 804, 814, 824 of further text culture projects (batch 6, 7 and 8) performed as described for the test batches depicted in FIGS. 5, 6 and 7. Online and offline cell density values are plotted in logarithmic scale, temperature in linear scale. The vertical arrows indicate the target time at which target cell density, e.g. 4,000,000 cells per ml (horizontal line) should be reached. FIG. 8 shows that the respective target time density was reached at the desired target time with good accuracy.

Batches 6, 7 and 8 basically have the same starting conditions, the same target cell density, but different target times. The respective target was reached almost exactly. The temperature profiles of the batches, in particular batch 8, shows that the control logic is capable of taking into account the current growth rates of the cells and thus, if appropriate, also the different growth phases (growth phase, stationary phase, or transient phase after inoculation).

FIG. 9 shows the online cell densities 902, 912, 922, the occasionally measured offline cell density values (symbols) 900, 910, 920, and the temperature signal (dashed lines) 904, 914, 924 of further text culture projects (batches 9 and 10) performed as described for the test batches depicted in FIGS. 5, 6 and 7. The plot is generated as described for FIG. 8 and comprises, as a reference, also the values for batch 8 (with different reference numbers 900, 902 and 904 rather than 820, 822 and 824). Batch 9 as a cell culture project that is designed to reproduce the target time and target cell density of batch 8 (3 days of length) although the temperatures of the plot reveal that at the time of inoculation, the media of batches 8 and 9 had different temperatures. Nevertheless, the program logic is able to provide the target cell density at the target time both for batch 8 and for batch 9 highly accurately.

Batch 10 was started with the same target cell density and starting temperature like batch 9, but with a different target time (4 days). With the result from batch 10, it could be shown that the same target cell density could be achieved with an entire day offset, with the same cell density as in batch 9. Thus, embodiments of the invention allow to clearly define the end point of the fermentation in a window of at least one day, e.g. to perform the inoculation of the subsequent fermenter at an appropriate time and to plan all preparations.

The above tests were performed with the cell line T074OPT B048WCB. Further tests were performed based on cell cultures of the CHO-cell line T072. In the further test cell culture projects, the duration of the adjustment interval (60-120 min), the starting cell densities, target times (about 3-4 days, or 67-95 hours) and the height of the temperature change (0.2-0.5° C.) were slightly varied. In all cell lines, the target cell density could be reached in the target time. All temperature curves were observed to differ from each other. Thus, the growth control system controlled each cell culture individually and successfully. In the event of major temperature adjustments, e.g. of 0.5-1.0° C., the length of the adjustment interval was increased (preferentially to at least 90 minutes) so that the cells have more time to adapt to the new temperature.

FIGS. 10-15 show that the growth control via temperature adjustment performed in accordance with embodiments of the invention allow to provide a desired cell density at a target time even though the cell culture projects may face one or more technical problems and failures during the project.

Technical disturbances can seriously jeopardize the success of a cell culture project. Typically, corrective actions are performed manually as soon as possible. Typically, an operation fault can be remedied within 4 hours. However, the delay in cell growth caused by the technical failure often resulted in a prolonged duration of the whole cell culture project.

In a set of tests, the ability of the control logic to compensate delays in cell growth caused by typical technical failures was evaluated by simulating a failure of one or more regulative controls of the bioreactors. The tested failure scenarios comprised a failure of the oxygen supply, failure of the oxygen electrode, failure of temperature control, failure of the pH control (CO2 supply) and others. In each of the tests, one or more control functionalities (e.g. O2 partial pressure regulation, CO2 partial pressure regulation, etc.) were stopped for 4 hours or an operative parameter (e.g. pH) was set to an undesirable value for approx. 4 hours. Then the control functionalities were re-activated or the operative parameters were re-set to a desirable or typical value. The settings of the control logic, in particular the target time and target cell density, were not changed during said tests.

The results of some of the tests are presented in the form of plots in FIGS. 10-15. The cell cultures used for said tests which are depicted in FIGS. 10-15 were grown as described for the cell cultures mentioned in the figure description of FIG. 5. The numbering of the cell cultures ("batches") used for said tests start here from the beginning. So the cell cultures 4-9 in FIGS. 10-15 are not identical to the cell cultures whose data forms the basis for FIGS. 5-9.

FIGS. 10 and 11 respectively depict two plots illustrating the capability of the control logic to compensate for a failure of oxygen supply. The testing of the control logic's ability to compensate for oxygen supply failures was made by deactivating the oxygen regulator during the time interval 48 h-52 h (FIG. 10) or during the time interval 55 h-59 h (FIG. 11). FIGS. 10 and 11 clearly show that the cells do not grow any more (oxygen signal) without oxygen (upper plots, decreased slope of cell density curve). The control logic determines a decreased growth rate, predicts that the cell density at target time will be below the target cell density given the low growth rate and raises the temperature with a delay of 1-2 h (lower plots in FIGS. 10 and 11). Despite the temporary fail of the oxygen supply, it was possible to achieve the desired cell density at the set target time.

FIGS. 12 and 13 respectively depict two plots illustrating the capability of the control logic to compensate for a failure of pH control and for a resulting undesirable pH value. The testing of the control logic's ability to compensate for pH control failures was made by abruptly changing the setpoint of the pH control to an undesirable value during the time interval 48 h-52 h (FIG. 12) or during the time interval 72 h-76 h (FIG. 13). FIGS. 12 and 13 shows that the pH change does not have a large effect on the growth of the cells and, as a consequence, the control logic does not have any problems to compensate for the pH induced growth effects and to provide the target cell density at the target time.

FIG. 14 depicts three plots illustrating the capability of the control logic to compensate for a failure of both oxygen supply and pH control. Again, the control logic was able to provide the target cell density at the target time.

FIG. 15 depicts two plots illustrating the capability of the control logic to compensate for a failure of both oxygen supply and temperature control. 26 hours after inoculation, failure of the oxygen supply was simulated for about 4 hours. The system reacted very strongly as expected to compensate for the reduced cell growth. The control logic reacted to the reduced oxygen supply by increasing the temperature during the time of failure. Approximately 12 hours later a temperature control failure was simulated by turning off the temperature regulator. In a time of about 4 hours the reactor temperature dropped to a value between 30 and 31° C. During this time, the control logic continues to predict future cell densities and compares the computed densities with the target cell density, but cannot pass and enforce the respective new temperature setpoints successfully. After the temperature controller was turned on again, the temperature controller received the new temperature setpoints from the control logic. This resulted in a slight overflow of the actual temperature, which is then quickly compensated for. During the remaining batch runtime, the cell culture was grown in a controlled manner. Again, the control logic was able to provide the target cell density at the target time.

Thus, it was successfully demonstrated that the temperature-based growth regulation according to embodiments of the invention is robust against and can compensate for various technical problems and failures. An intermittent failure of the oxygen or pH control is tolerated without problems and its effects on the growth are compensated for. Even a failure of the temperature control can still be absorbed.

The invention claimed is:

1. A method for controlling growth of eukaryotic cells, the method comprising:

receiving, by a control logic, a target cell density and a target time, the target cell density representing a desired cell density of the eukaryotic cells at the target time, the target time representing a future point in time;

cultivating the eukaryotic cells in a culture medium of a first tank for a plurality of time intervals;

for each of the plurality of time intervals:

measuring a cell density of the eukaryotic cells in the culture medium;

computing, by the control logic, a predicted cell density at the target time as a function of at least one measurement of the measured cell density at a current time interval of the plurality of time intervals;

comparing, by the control logic, the predicted cell density to the target cell density; and adjusting, by the control logic, a temperature of the culture medium in the first tank if the predicted cell density deviates from the target cell density by increasing the temperature by 0.1° C. to 1° C. if the predicted cell density is lower than the target cell density, or decreasing the temperature by 0.1° C. to 1° C. if the predicted cell density is higher than the target cell density.

2. The method of claim 1, the first tank comprising a meter for performing online measurements of the cell density in the culture medium, the cell densities of the eukaryotic cells measured at each of the plurality of time intervals being online-measurements.

3. The method of claim 1, further comprising:

automatically terminating, by the control logic, at least the adjusting of the temperature upon a termination criterion being fulfilled, the termination criterion being one of:

the target time has been reached; or the measured cell density is equal to or larger than the target cell density.

4. The method of claim 1, further comprising:

providing, by the control logic to a display coupled to the control logic, a graphical user interface-GUI, the GUI enabling a user to enter the target time and the target cell density before the control logic starts to compute the predicted cell densities, the GUI enabling the user to modify the target time and/or the target cell density while the control logic computes the predicted cell densities at the plurality of time intervals.

5. The method of claim 1, further comprising:

after the target cell density was reached, transferring the culture medium of the first tank and the eukaryotic cells contained therein from the first tank to a second tank, the second tank being larger than the first tank;

receiving, by the control logic, a further target cell density and a further target time, the further target cell density representing a desired cell density of the eukaryotic cells at the further target time, the further target time representing a future point in time;

cultivating the transferred eukaryotic cells in the second tank;

for each of a plurality of further time intervals:

measuring the cell density of the eukaryotic cells in a culture medium of the second tank;

computing, by the control logic, a further predicted cell density at the further target time as a function of at least said measured cell density;

comparing, by the control logic, the further predicted cell density and the further target cell density; and adjusting, by the control logic, the temperature of the culture medium in the second tank if the further predicted cell density deviates from the further target cell density by increasing the temperature by 0.1° C. to 1° C. if the further predicted cell density is lower than the further target cell density; or decreasing the temperature by 0.1° C. to 1° C. if the further predicted cell density is higher than the further target cell density.

6. The method of claim 5, the first tank being a bioreactor configured for growing the cell culture as batch-culture, the second tank being larger than the first tank and being a bioreactor configured for growing the cell culture as batch-culture, the method being used in a seed train cultivation process for generating a defined minimum number of cells for inoculation of a production bioreactor.

7. The method of claim 1, the eukaryotic cells being mammalian cells.

8. The method of claim 1, the method further comprising:

for each of the plurality of time intervals:

defining a current observation interval for the current time interval, the current observation interval having a predefined length and terminating at an end of the current time interval; and receiving all cell densities having been measured during the current observation interval, wherein the computing of the predicted cell density as the function of at least the measured cell density at the current time interval comprises extrapolating the cell densities measured during the current observation interval until the target time.

9. The method of claim 8, the extrapolation comprising performing a curve fitting operation or a regression analysis on the cell densities measured during the current observation interval.

10. The method of claim 1, the plurality of time intervals being of equal length.

11. The method of claim 1, the method further comprising:

determining if the current time interval is close to the target time based on whether a predefined duration of time has elapsed since inoculation of the culture medium, a predefined number of predications of the cell density has been performed, a predefined percentage of the target cell density has been reached, or a predefined time prior to the target time has been reached; and in response to determining that the current time is close to the target time, reducing a length of all future ones of the plurality of time intervals.

12. The method of claim 8, the predefined length of the observation interval being in a range of 60 minutes to 480 minutes.

13. The method of claim 1, the adjusting of the temperature comprising increasing the temperature by 0.1° C. to 0.5° C., or decreasing the temperature by 0.1° C. to 0.5° C.

14. The method of claim 1, the control logic performing the temperature adjustment of the first tank only in a case where at least an adjustment time interval has lapsed since a previous temperature adjustment of said first tank, a duration of the adjustment time interval being in a range of 60-120 minutes.

15. The method of claim 7, wherein the eukaryotic cells are Chinese hamster ovary cells.

16. The method of claim 13, wherein the adjusting of the temperature includes increasing the temperature by 0.1° C. to 0.2° C., or decreasing the temperature by 0.1° C. to 0.2° C.

* * * * *